US009205047B2

(12) United States Patent
Shoichet et al.

(10) Patent No.: US 9,205,047 B2
(45) Date of Patent: *Dec. 8, 2015

(54) TUNABLE SUSTAINED RELEASE OF A SPARINGLY SOLUBLE HYDROPHOBIC THERAPEUTIC AGENT FROM A HYDROGEL MATRIX (75) Inventors: Molly S. Shoichet, Toronto (CA); Yakov Lapitsky, Toledo, OH (US); Yuanfei Wang, Toronto (CA)

(73) Assignee: The Governing Council of the University of Toronto, Toronto, Ontario (CA)

( * ) Notice: Subject to any disclaimer, the term of this patent is extended or adjusted under 35 U.S.C. 154(b) by 133 days.

This patent is subject to a terminal disclaimer.

(21) Appl. No.: 12/785,083

(22) Filed: May 21, 2010

(65) Prior Publication Data

US 2010/0291191 A1 Nov. 18, 2010

Related U.S. Application Data (63) Continuation-in-part of application No. 11/410,831, filed on Apr. 25, 2006, now Pat. No. 7,767,656.

(60) Provisional application No. 60/674,299, filed on Apr. 25, 2005.

(51) Int. Cl.
| | |
|---|---|
| A61K 9/127 | (2006.01) |
| A61K 9/14 | (2006.01) |
| A61P 29/00 | (2006.01) |
| A61P 33/10 | (2006.01) |
| A61P 9/06 | (2006.01) |
| A61P 31/04 | (2006.01) |
| A61P 25/24 | (2006.01) |
| A61P 7/02 | (2006.01) |
| A61P 31/00 | (2006.01) |
| A61P 25/06 | (2006.01) |
| A61P 35/00 | (2006.01) |
| A61P 33/02 | (2006.01) |
| A61P 25/16 | (2006.01) |
| A61P 3/02 | (2006.01) |
| A61K 31/4418 | (2006.01) |
| A23L 1/00 | (2006.01) |
| A61K 9/00 | (2006.01) |
| A61K 47/36 | (2006.01) |
| A61K 47/38 | (2006.01) |

(52) U.S. Cl.
CPC ............... *A61K 9/0024* (2013.01); *A61K 9/14* (2013.01); *A61K 47/36* (2013.01); *A61K 47/38* (2013.01)

(58) Field of Classification Search
CPC ....... A61K 9/0024; A61K 9/14; A61K 47/38; A61K 47/36
USPC .............. 424/450, 488; 426/658, 89; 514/356
See application file for complete search history.

(56) References Cited

U.S. PATENT DOCUMENTS

| | | | | |
|---|---|---|---|---|
| 5,851,229 | A * | 12/1998 | Lentz et al. | 623/23.72 |
| 6,063,405 | A | 5/2000 | Drizen et al. | |
| 6,335,035 | B1 | 1/2002 | Drizen et al. | |
| 6,462,093 | B1 * | 10/2002 | Miyamoto et al. | 514/772.3 |
| 6,586,493 | B1 | 7/2003 | Massia | |
| 6,656,502 | B1 * | 12/2003 | Hara et al. | 424/464 |
| 6,692,766 | B1 | 2/2004 | Rubinstein et al. | |
| 6,716,251 | B1 | 4/2004 | Asius et al. | |
| 2005/0095267 | A1 * | 5/2005 | Campbell et al. | 424/425 |
| 2005/0119219 | A1 * | 6/2005 | Bellini et al. | 514/54 |
| 2006/0280797 | A1 * | 12/2006 | Shoichet et al. | 424/486 |
| 2009/0220497 | A1 * | 9/2009 | Brown et al. | 424/133.1 |

OTHER PUBLICATIONS

Wang et al. (Journal of Controlled Release 2009, 140, 218-223 available online on May 23, 2009).*
Lin et al. (Chin. J. Chem. Eng 2007, 15(4), 566-572).*
Banerjee et al. (International Journal of Biomaterials 2009, 9 pages).*
Machine Translation of JP2003-342197.*
DailyMed—"Ibuprofen." Retrieved on Apr. 21, 2014. Retrieved from the internet <URL:http://dailymed.nlm.nih.gov/dailymed/lookup.cfm?setid=23dc7eeb-0b0a-4a11-9783-fdba769309cd#nlm34089-3>.*
Arun, A., B.S.R. Reddy, in vitro drug release studies from the polymeric hydrogels based on HEA and HPMA using 4-{(E)-[(3Z)-3-(4-(acryloyloxy)benzylidene)-2-hexylidene]methyl}lphenyl acrylate as a crosslinker. Biomaterials 26(10) (2005) 1185-1193.
Yoshida, A., M. Yamamoto, T. Itoh, T. Irie, F. Hirayama, K. Uekama, Utility of 2-Hydroxypropyl-Beta-Cyclodextrin in an Intramuscular Injectable Preparation of Nimodipine. Chemical & Pharmaceutical Bulletin 38(1) (1990) 176-179.
Brazel, C.S., N.A. Peppas, Modeling of drug release from swellable polymers. Eur J Pharm Biopharm 49(1) (2000) 47-58.
Cabrera, M.I., J.A. Luna, R.J.A. Grau, Modeling of dissolution-diffusion controlled drug release from planar polymeric systems with finite dissolution rate and arbitrary drug loading. Journal of Membrane Science 280(1-2) (2006) 693-704.
Chenite, A., Chaput, C., Wang, D. Combes, C., Buschmann, M.D., Hoemann, C. D., Leroux, J. C., Atkinson, B. L., Atkinson, B. L., Binette, F., Selmani, A., Novel Injectable Neutral Solutions of Chitosan Form Biodegradable Gels in Situ, Biomaterials 21, (2000), pp. 2155-2161.
Gbor, P.K., C.Q. Jia, Critical evaluation of coupling particle size distribution with the shrinking core model. Chemical Engineering Science 59(10) (2004) 1979-1987.
Gupta, D., C.H. Tator, M.S. Shoichet, Fast-gelling injectable blend of hyaluronan and methylcellulose for intrathecal, localized delivery to the injured spinal cord. Biomaterials 27(11) (2006) 2370-2379.

(Continued)

Primary Examiner — Anoop Singh
Assistant Examiner — Doan Phan
(74) Attorney, Agent, or Firm — Price Heneveld LLP (57) ABSTRACT The incorporation of polymeric excipients into an injectable hydrogel matrix, for example, methyl cellulose in the case of a hydrogel matrix comprising hyaluronan and methylcellulose (HAMC) has been found to increase the solubility of sparingly soluble hydrophobic drugs and tune their rate of release. The hydrogel matrix may also include other sparingly soluble hydrophobic food or cosmetic agents.

18 Claims, 3 Drawing Sheets

(56) References Cited

OTHER PUBLICATIONS

Hancock, B.C., M. Parks, What is the true solubility advantage for amorphous pharmaceuticals? Pharmaceut Res 17 (4) (2000) 397-404.

He, Z.G., D.F. Zhong, X.Y. Chen, X.H. Liu, X. Tang, L.M. Zhao, Development of a dissolution medium for nimodipine tablets based on bioavailability evaluation. Eur J Pharm Sci 21(4) (2004) 487-491.

Higuchi, W.I., Diffusional Models Useful in Biopharmaceutics—Drug Release Rate Processes. J Pharm Sci 56(3) (1967) 315-324.

Hixson, A.W., J.H. Crowell, Dependence of reaction velocity upon surface and agitation I—Theoretical consideration. Industrial and Engineering Chemistry 23 (1931) 923-931.

Hoffman, Allan S., Bioconjugates of Intelligent Polymers and Recognition Proteins for Use in Diagnostics and Affinity Separations, Clinical Chemistry, (2000), v. 46:9, pp. 1478-1486.

Kang, C. E, Poon PC, Tator CH, Shoichet MS, A New Paradigm for Local and Sustained Release of Therapeutic Molecules to the Injured Spinal Cord for Neuroprotection and Tissue Repair. Tissue Engineering Part A 15(3) (2009) 595-604.

Kim, Mee Ryan, Park, Tae Gwan, Temperature-responsive and Degradable Hyaluronic Acid/Pluronic Composite Hydrogels for Controlled Release of Human Growth Hormone, Journal of Controlled Release, (2002), v. 80, pp. 69-77.

Kotiyan, P.N., P.R. Vavia, Eudragits: Role as crystallization inhibitors in drug-in-adhesive transdermal systems of estradiol. Eur J Pharm Biopharm 52(2) (2001) 173-180.

Krieglstein, J., Excitotoxicity and neuroprotection. Eur J Pharm Sci 5(4) (1997) 181-187.

Krishnaiah, Y.S.R., P. Bhaskar, V. Satyanarayana, Penetration-enhancing effect of ethanol-water solvent system and ethanolic solution of carvone on transdermal permeability of nimodipine from HPMC gel across rat abdominal skin. Pharmaceutical Development and Technology 9(1) (2004) 63-74.

Kumprakob, U., J. Kawakami, I. Adachi, Permeation enhancement of ketoprofen using a supersaturated system with antinucleant polymers. Biological & Pharmaceutical Bulletin 28(9) (2005) 1684-1688.

Liang, Hsiang-Fa, Hong, MiN-Hao, Ho, Rong-Ming, Chung, Ching-Kuang, Lin, Yu-Hsin, Chen, Chun-Hung, Sung, Hsing-Wen, Novel Method Using a Temperature-Sensitive Polymer (Methylcellulose) to Thermally Gel Aqueous Alginate as a pH-Sensitive Hydrogel, Biomacromolecules, 2004, v. 5, pp. 1917-1925.

Lin, C.C., A.T. Metters, Hydrogels in controlled release formulations: Network design and mathematical modeling. Adv Drug Deliver Rev 58(12-13) (2006) 1379-1408.

Lu, E., Z.Q. Jiang, Q.Z. Zhang, X.G. Jiang, A water-insoluble drug monolithic osmotic tablet system utilizing gum arabic as an osmotic, suspending and expanding agent. J Control Release 92(3) (2003) 375-382.

Ma, X.G., J. Taw, C.M. Chiang, Control of drug crystallization in transdermal matrix system. Int J Pharm 142(1) (1996) 115-119.

Matteucci, M.E., B.K. Brettmann, T.L. Rogers, E.J. Elder, R.O. Williams, K.P. Johnston, Design of potent amorphous drug nanoparticles for rapid generation of highly supersaturated media. Molecular Pharmaceutics 4(5) (2007) 782-793.

Nalluri, B.N., C. Milligan, J.H. Chen, P.A. Crooks, A.L. Stinchcomb, in vitro release studies on matrix type transdermal drug delivery system of naltrexone and its acetyl prodrug. Drug Dev Ind Pharm 31(9) (2005) 871-877.

Norenberg, M.D., J. Smith, A. Marcillo, The pathology of human spinal cord injury: Defining the problems. J Neurotrauma 21(4) (2004) 429-440.

Ohya, Shoji, Nakayama, Yasuhide, Matsuda, Takehisa, Thermoresponsive Artificial Extracellular Matrix for Tissue Engineering: Hyaluronic Acid Bioconjugated With Poly(N-isopropylacrylamide) Grafts, Biomacromolecules, (2001), v. 2, pp. 856-863.

Peppas, N.A., A Model of Dissolution-Controlled Solute Release from Porous Drug Delivery Polymeric Systems. Journal of Biomedical Materials Research 17(6) (1983) 1079-1087.

Raghavan, S.L., A. Trividic, A.F. Davis, J. Hadgraft, Crystallization of hydrocortisone acetate: influence of polymers. Int J Pharm 212(2) (2001) 213-221.

Raghavan, S.L., A. Trividic, A.F. Davis, J. Hadgraft, Effect of cellulose polymers on supersaturation and in vitro membrane transport of hydrocortisone acetate. Int J Pharm 193(2) (2000) 231-237.

Raghavan, S.L., K. Schuessel, A. Davis, J. Hadgraft, Formation and stabilisation of triclosan colloidal suspensions using supersaturated systems. Int J Pharm 261(1-2) (2003) 153-158.

Rao, V.M., J.L. Haslam, V.J. Stella, Controlled and complete release of a model poorly water-soluble drug, prednisolone, from hydroxypropyl methylcellulose matrix tablets using (SBE)(7M)-beta-cyclodextrin as a solubilizing agent. J Pharm Sci 90(7) (2001) 807-816.

Scriabine, A., T. Schuurman, J. Traber, Pharmacological Basis for the Use of Nimodipine in Central Nervous-System Disorders. Faseb J 3(7) (1989) 1799-1806.

Siepmann, J., N.A. Peppas, Modeling of drug release from delivery systems based on hydroxypropyl methylcellulose (HPMC). Adv Drug Deliver Rev 48(2-3) (2001) 139-157.

Silver, Frederick H., Librizzi, Joseph, Pins, George, Wang, Ming-Che, Benedetto, Dominick, Physical Properties of Hyaluronic Acid and Hydroxypropylmethylcellulose in Solution: Evaluation of Coating Ability, Journal of Applied biomaterials, (1994), v. 5, pp. 89-98.

Tate, Matthew c., Shear, Deborah A., Hoffman, Stuart W., Stein, Donald G., and Laplaca, Michelle C., Biocompatibility of Methylcellulose-based Constructs Designed for Intracerebral Gelation Following Experimental Traumatic Brain Injury, Biomaterials 22, (2001), pp. 1113-1123.

Tator, C.H., Strategies for recovery and regeneration after brain and spinal cord injury. Injury Prevention 8 (2002) Iv33-Iv36.

Zema, L., Maroni, A., Foppoli, A., Palugan, L., Sangalli, M.E., Gazzaniga, A., Different HPMC viscosity grades as coating agents for an oral time and/or site-controlled delivery system: An investigation into the mechanisms governing drug release. J Pharm Sci 96(6) (2007) 1527-1536.

Velikov, K.P., E. Pelan, Colloidal delivery systems for micronutrients and nutraceuticals. Soft Matter 4(10) (2008) 1964-1980.

Wen, H., K.R. Morris, K. Park, Synergic effects of polymeric additives on dissolution and crystallization of acetaminophen. Pharmaceut Res 25(2) (2008) 349-358.

Wen, Hong, Morris, Kenneth R., Park, Kinam, Hydrogen Bonding Interactions Between Adsorbed Polymer Molecules and Crystal Surface of Acetaminophen, Journal of Colloid and Interface Science 290, (2005), pp. 325-335.

Xu, Y., Wang, C., Tam, K. C., Li,L., Salt-Assisted and Salt-Suppressed Sol-Gel Transitions of Methylcellulose in Water, Langmuir (2004), v. 20, pp. 646-652.

Yamashita, K., T. Nakate, K. Okimoto, A. Ohike, Y. Tokunaga, R. Ibuki, K. Higaki, T. Kimura, Establishment of new preparation method for solid dispersion formulation of tacrolimus. Int J Pharm 267(1-2) (2003) 79-91.

* cited by examiner

TUNABLE SUSTAINED RELEASE OF A SPARINGLY SOLUBLE HYDROPHOBIC THERAPEUTIC AGENT FROM A HYDROGEL MATRIX

CROSS REFERENCE TO RELATED APPLICATIONS

This application is a continuation in part of U.S. patent application Ser. No. 11/410,831, filed Apr. 25, 2006 now U.S. Pat. No. 7,767,656, which application claims benefit to U.S. Provisional Application Ser. No. 60/674,299, filed Apr. 25, 2005, both of which are incorporated herein by reference in their entirety.

FIELD OF THE INVENTION

The incorporation of polymeric excipients into an injectable hydrogel matrix, for example, methyl cellulose in the case of a hydrogel matrix comprising hyaluronan and methylcellulose (HAMC) has been found to increase the solubility of sparingly soluble hydrophobic drugs and tune their rate of release. The hydrogel matrix may also include other sparingly soluble hydrophobic food or cosmetic agents.

BACKGROUND OF THE INVENTION

Traumatic spinal cord injury (SCI) is a devastating condition for which there is no cure. Currently, there is no standard of care for traumatic brain injury or stroke. There is also no cure for stroke, and the only FDA approved treatment is tissue plasminogen activator (tPA), a thrombolytic agent with limited therapeutic benefit [*Stroke and cerebrovascular accidents*. World Health Organization, Circulation, 2009]. There is a need generally to provide therapies for all traumatic injuries to the central nervous system. The initial mechanical trauma, termed the primary injury, causes damage to blood vessels and localized cell death [C. H. Tator, Strategies for recovery and regeneration after brain and spinal cord injury. Injury Prevention 8 (2002) Iv33-Iv36.]. These in turn lead to excitotoxicity, inflammation, hemorrhage, vasospasm, and edema, which result in functional deficits in the patient [J. Krieglstein, Excitotoxicity and neuroprotection. Eur J Pharm Sci 5(4) (1997) 181-187; A. Scriabine, T. Schuurman, J. Traber, Pharmacological Basis for the Use of Nimodipine in Central Nervous- System Disorders. Faseb J 3(7) (1989) 1799-1806]. These pathological events can occur from days to months after injury and are known as the secondary injury [A. Arun, B. S. R. Reddy, In vitro drug release studies from the polymeric hydrogels based on HEA and HPMA using 4-{(E)-[(3Z)-3-(4-(acryloyloxy)benzylidene)-2-hexylidene] methyl}lphenyl acrylate as a crosslinker. Biomaterials 26(10) (2005) 1185-1193; M. D. Norenberg, J. Smith, A. Marcillo, *The pathology of human spinal cord injury: Defining the problems*. J Neurotraum 21(4) (2004) 429-440]. Both neuroregenerative and neuroprotective therapeutics are being pursued to limit the devastation that occurs after injury, yet their delivery remains challenging.

There are three common delivery strategies—systemic, pump/catheter, and bolus—yet each has its drawbacks. Systemic delivery is limited because most molecules cannot cross the blood-spinal cord barrier and those that do may have profound systemic side effects [C. H. Tator, *Strategies for recovery and regeneration after brain and spinal cord injury*. Injury Prevention 8 (2002) Iv33-Iv36]. The external pump/catheter system pumps drugs from a reservoir into the intrathecal space through a catheter. While a constant dose can be administered, this method is open to infection and has not been approved for long-term delivery in SCI patients in the USA. Bolus injection into the intrathecal space is compromised by cerebral spinal fluid (CSF) flow, which disperses the drug, thereby requiring repeated administration.

Much research effort has been devoted to improving the therapeutic efficacy and delivery of hydrophobic drugs which is often limited by low solubility [L. Zema, A. Maronii, A. Foppoli, L. Palugan, M. E. Sangalli, A. Gazzaniga, Different HPMC viscosity grades as coating agents for an oral time and/or site-controlled delivery system: An investigation into the mechanisms governing drug release. *J Pharm Sci* 96(6) (2007) 1527-1536; Z. G. He, D. F. Zhong, X. Y. Chen, X. H. Liu, X. Tang, L. M. Zhao, Development of a dissolution medium for nimodipine tablets based on bioavailability evaluation. *Eur J Pharm Sci* 21(4) (2004) 487-491; E. Lu, Z. Q. Jiang, Q. Z. Zhang, X. G. Jiang, A water-insoluble drug monolithic osmotic tablet system utilizing gum arabic as an osmotic, suspending and expanding agent. *J Control Release* 92(3)(2003) 375-382]. In solid pharmaceutical formulations, polymeric excipients similar to MC, such as hydroxypropyl methylcellulose or poly(vinylpyrrolidone), are incorporated into the drug particles to increase the solubility of sparingly soluble drugs [Z. G. He, D. F. Zhong, X. Y. Chen, X. H. Liu, X. Tang, L. M. Zhao, Development of a dissolution medium for nimodipine tablets based on bioavailability evaluation. *Eur J Pharm Sci* 21(4) (2004) 487-491; H. Wen, K. R. Morris, K. Park, Synergic effects of polymeric additives on dissolution and crystallization of acetaminophen. *Pharmaceut Res* 25(2) (2008) 349-358; B. C. Hancock, M. Parks, What is the true solubility advantage for amorphous pharmaceuticals? *Pharmaceut Res* 17(4) (2000) 397-404; M. E. Matteucci, B. K. Brettmann, T. L. Rogers, E. J. Elder, R. O. Williams, K. P. Johnston, Design of potent amorphous drug nanoparticles for rapid generation of highly supersaturated media. *Molecular Pharmaceutics* 4(5) (2007) 782-793; S. L. Raghavan, A. Trividic, A. F. Davis, J. Hadgraft, Crystallization of hydrocortisone acetate: influence of polymers. *Int J Pharm* 212(2) (2001) 213-221]. This is typically achieved by disrupting the crystalline drug particle structure [B. C. Hancock, M. Parks, What is the true solubility advantage for amorphous pharmaceuticals? *Pharmaceut Res* 17(4) (2000) 397-404; M. E. Matteucci, B. K. Brettmann, T. L. Rogers, E. J. Elder, R. O. Williams, K. P. Johnston, Design of potent amorphous drug nanoparticles for rapid generation of highly supersaturated media. *Molecular Pharmaceutics* 4(5) (2007) 782-793], thereby producing a less-stable amorphous drug particle that can be up to orders of magnitude more soluble than the crystalline drug [B. C. Hancock, M. Parks, What is the true solubility advantage for amorphous pharmaceuticals? *Pharmaceut Res* 17(4) (2000) 397-404; M. E. Matteucci, B. K. Brettmann, T. L. Rogers, E. J. Elder, R. O. Williams, K. P. Johnston, Design of potent amorphous drug nanoparticles for rapid generation of highly supersaturated media. *Molecular Pharmaceutics* 4(5) (2007) 782-793; V. M. Rao, J. L. Haslam, V. J. Stella,Controlled and complete release of a model poorly water-soluble drug, prednisolone, from hydroxypropyl methylcellulose matrix tablets using (SBE)(7M)-beta-cyclodextrin as a solubilizing agent. J Pharm Sci 90(7) (2001) 807-816]. These polymeric excipients are also used as stabilizing additives in supersaturated solutions [M. E. Matteucci, B. K. Brettmann, T. L. Rogers, E. J. Elder, R. O. Williams, K. P. Johnston, Design of potent amorphous drug nanoparticles for rapid generation of highly supersaturated media. *Molecular Pharmaceutics* 4(5) (2007) 782-793; S. L. Raghavan, A. Trividic, A. F. Davis, J. Hadgraft,Crystallization of hydrocortisone acetate: influence of polymers. *Int J Pharm* 212(2)

(2001) 213-221; S. L. Raghavan, A. Trividic, A. F. Davis, J. Hadgraft, Effect of cellulose polymers on supersaturation and in vitro membrane transport of hydrocortisone acetate. *Int J Pharm* 193(2) (2000) 231-237; K. Yamashita, T. Nakate, K. Okimoto, A. Ohike, Y. Tokunaga, R. Ibuki, K. Higaki, T. Kimura, Establishment of new preparation method for solid dispersion formulation of tacrolimus. *Int J Pharm* 267(1-2) (2003) 79-91; S. L. Raghavan, K. Schuessel, A. Davis, J. Hadgraft, Formation and stabilisation of triclosan colloidal suspensions using supersaturated systems. *Int J Pharm* 261 (1-2) (2003) /153-158; U. Kumprakob, J. Kawakami, I. Adachi, Permeation enhancement of ketoprofen using a supersaturated system with antinucleant polymers. *Biological & Pharmaceutical Bulletin* 28(9) (2005) 1684-1688] and gels [S. L. Raghavan, A. Trividic, A. F. Davis, J. Hadgraft, Crystallization of hydrocortisone acetate: influence of polymers. *Int J Pharm* 212(2) (2001) 213-221; S. L. Raghavan, A. Trividic, A. F. Davis, J. Hadgraft, Effect of cellulose polymers on supersaturation and in vitro membrane transport of hydrocortisone acetate. *Int J Pharm* 193(2) (2000) 231-237] for oral and transdermal drug delivery, where a layer of adsorbed, "antinucleating" polymer on the surface of the nascent crystal is believed to inhibit further crystallization of the drug [X. G. Ma, J. Taw, C. M. Chiang, Control of drug crystallization in transdermal matrix system. *Int J Pharm* 142(1) (1996) 115-119; P. N. Kotiyan, P. R. Vavia, Eudragits: Role as crystallization inhibitors in drug -in-adhesive transdermal systems of estradiol. *Eur J Pharm Biopharm* 52(2) (2001) 173-180].

Given the limitations associated with current delivery strategies as described previously, a minimally-invasive injectable, thermally-responsive hydrogel comprised of hyaluronan (HA) and methylcellulose (MC) was designed for sustained and localized release. [D. Gupta, C. H. Tator, M. S. Shoichet, Fast-gelling injectable blend of hyaluronan and methylcellulose for intrathecal, localized delivery to the injured spinal cord. *Biomaterials* 27(11) (2006) 2370-2379]. This physical blend has been shown to be safe and provide greater neuroprotection when used to deliver erythropoietin to the intrathecal space than traditional delivery strategies such as intraperitoneal and intrathecal bolus [Kang C E, Poon P C, Tator C H, Shoichet M S, A New Paradigm for Local and Sustained Release of Therapeutic Molecules to the Injured Spinal Cord for Neuroprotection and Tissue Repair. *Tissue Engineering Part A* 15(3) (2009) 595-604].

U.S. parent patent application Ser. No. 11/410,831 describes a polymer blend comprising an inverse thermal gelling polymer and an anionic polymer, for example HAMC that exists as a gel. This polymer mixture has a shorter time to gelation than the inverse gelling polymer alone, and may be used alone or as a drug delivery vehicle for many applications. In particular, the polymer mixture can be used for localized, targeted delivery of pharmaceutical agents upon injection providing sustained release. A particular use of this polymer mixture is in delivery of a therapeutic agent in a highly localized, targeted manner, wherein the polymer matrix-contained therapeutic agent is able to circumvent the blood-spinal cord barrier or blood-brain barrier and enter the target tissue directly. This can be achieved, for example, by injection of the matrix (or mixture) into the intrathecal space, a fluid-filled space wherein cerebral spinal fluid flows. U.S. Pat. No. 6,335,035 ('035) to Drizen, et al. is a divisional of U.S. Pat. No. 6,063,405 to Drizen et al. which teaches sustained release compositions comprising a drug dispersed within a polymer matrix, methods of producing the same and treatments with the complex. The '035 patent discloses a sustained drug delivery system, which comprises a drug dispersed within a polymer matrix solubilized or suspended in a polymer matrix. The polymer matrix is composed of a highly negatively charged polymer material selected from the group consisting of polysulfated glucosoglycans, glycoaminoglycans, mucopolysaccharides and mixtures thereof, and a non-ionic polymer selected from the group consisting of carboxymethylcellulose sodium, hydroxypropylcellulose and mixtures thereof. Nonionic polymers are generally used in amounts of 0.1% to 1.0% and preferably from 0.5% to 1.0%. Nonionic polymers in amounts above 1.0% are not used as they result in the formation of a solid gel product when employed in combination with an anionic polymer.

U.S. Pat. No. 6,692,766 to Rubinstein et al. concerns a controlled release drug delivery system comprising a drug which is susceptible to enzymatic degradation by enzymes present in the intestinal tract; and a polymeric matrix which undergoes erosion in the gastrointestinal tract comprising a hydrogel-forming polymer selected from the group consisting of (a) polymers which are themselves capable of enhancing absorption of said drug across the intestinal mucosal tissues and of inhibiting degradation of said drug by intestinal enzymes; and (b) polymers which are not themselves capable of enhancing absorption of said drug across the intestinal mucosal tissues and of inhibiting degradation of said drug by intestinal enzymes.

U.S. Pat. No. 6,716,251 to Asius et al. discloses an injectable implant for filling up wrinkles, thin lines, skin cracks and scars for reparative or plastic surgery, aesthetic dermatology and for filling up gums in dental treatment. The invention concerns the use of biologically absorbable polymer microspheres or micro particles suspended in a gel.

U.S. Pat. No. 6,586,493 to Massia et al. discloses hyaluronate-containing hydrogels having angiogenic and vascularizing activity and pre-gel blends for preparing the hydrogels. The hydrogels contain a cross-linked matrix of a non-angiogenic hyaluronate and a derivatized polysaccharide material, in which cross-linking is effected by free-radical polymerization. JP2003-342197 discloses a heat gelling pharmaceutical preparation containing methylcellulose and hyaluronic acid that is liquid at room temperature and gels upon administration to the eye. The literature also teaches the properties of gel-forming polymer mixtures and their use as drug delivery vehicles (Xu et al. Langmuir, (2004) 20(3): 646-652, Liang et al. Biomacromolecules, 2004. 5(5):1917-25, Ohya et al. Biomacromolecules (2001) 2:856-863, Cho et al. International Journal of Pharmaceutics (2003) 260:83-91, Kim et al. Journal of Controlled Release (2002) 80:69-77, Tate et al. Biomaterials (2001) 22:1113-1123, and Silver et al., Journal of Applied Biomaterials (1994) 5:89-98).

SUMMARY OF THE INVENTION

Whether for the delivery of medical or non-medical applications, such as cosmetic or food applications, the delivery of hydrophobic molecules is difficult to achieve in water-based systems. Methyl cellulose itself solubilises the hydrophobic molecules (drugs or otherwise), thereby increasing the amount of hydrophobic molecule released. This is beneficial for the delivery of hydrophobic drugs for medical applications and hydrophobic molecules for cosmetic or food applications. The MC hydrogel may be used alone for this purpose—that is MC mixed with hydrophobic molecules—or MC may be used together with hyaluronan, an anionic polymer that lowers the gelation temperature of MC and allows the hydrogel blend to be shear-thinning. Importantly, other hydrophobic cellulose derivatives will be useful in solubilising hydrophobic molecules.

This disclosure relates to a hydrogel matrix comprising an aqueous mixture methylcellulose or other water soluble hydrophobic cellulose derivative, in which particles of at least one selected size of at least one sparingly soluble hydrophobic agent are dispersed and solubilised, which is blended with an anionic polysaccharide or a derivative thereof to form the hydrogel matrix, the solubility of the sparingly soluble hydrophobic agent being increased in the presence of the methylcellulose or other water soluble hydrophobic cellulose derivative, which together with the selected particle sizes determine the sustained release profile of the at least one sparingly soluble hydrophobic agent from the hydrogel matrix.

In another aspect, the disclosure provides a method for the manufacture of a hydrogel matrix as described above, wherein the matrix has a tunable therapeutic agent release profile comprising the steps of 1) providing particles of at least one selected size of the at least one sparingly soluble hydrophobic agent; 2) dispersing and solubilising the particles in an aqueous solution of methylcellulose or other water soluble hydrophobic cellulose derivative; and 3) blending the thus formed dispersion with an anionic polysaccharide or a derivative thereof to form the hydrogel matrix containing the at least one solubilised sparingly soluble hydrophobic agent; wherein, the solubility of the sparingly soluble hydrophobic agent is increased in the presence of the methylcellulose or other water soluble hydrophobic cellulose derivative which together with the selected particle sizes of the sparingly soluble hydrophobic agent determine the sustained release profile of the at least one sparingly soluble hydrophobic agent from the hydrogel matrix.

This disclosure also provides for a hydrogel matrix without the use of the anionic polysaccharide or a derivative thereof. In this form the hydrogel matrix comprises an aqueous mixture of methylcellulose or other water soluble hydrophobic cellulose derivative, in which particles of at least one selected size of at least one sparingly soluble hydrophobic agent are dispersed and solubilised, the solubility of the sparingly soluble hydrophobic agent being increased in the presence of the methylcellulose or other water soluble hydrophobic cellulose derivative, which together with the selected particle sizes determine the sustained release profile of the at least one sparingly soluble hydrophobic agent from the hydrogel matrix.

There is also disclosed in a related aspect, a method for the manufacture of a hydrogel matrix as described above, wherein the matrix has a tunable agent release profile comprising the steps of 1) providing particles of at least one selected size of the at least one sparingly soluble hydrophobic agent; 2) dispersing and solubilising the particles in an aqueous mixture of methylcellulose or other water soluble hydrophobic cellulose derivative; and 3) increasing the temperature of the thus formed solution to form the hydrogel matrix containing the at least one solubilised sparingly soluble hydrophobic therapeuti agent; wherein, the solubility of the sparingly soluble hydrophobic agent is increased in the presence of the methylcellulose or other water soluble hydrophobic cellulose derivative which together with the selected particle sizes of the sparingly soluble hydrophobic agent determine the sustained release profile of the at least one sparingly soluble hydrophobic agent from the hydrogel matrix.

While the primary purpose of the hydrogel matrix described herein is pharmaceutical, there are many sparingly soluble hydrophobic substances that can benefit from this form of delivery and administration, in applications such as cosmetics and food. In these forms, the hydrogel composite may also be used as a bulking agent for reconstructive or cosmetic surgery or as a lubricating agent, or matrix for in situ tissue growth. Because methylcellulose is currently used in food, the hydrogel composite could be used, for example in molecular gastronomy. Thus, the sparingly soluble hydrophobic agent may be selected from therapeutic, food and cosmetic agents, and combinations thereof.

DETAILED DESCRIPTION OF THE PREFERRED EMBODIMENT

The term "solubilization" as used herein is meant to have its ordinary meaning which is generally understood to be "to make a substance more soluble or soluble in water."

It is well-known in the art that MC gels as temperature increases. This gelation process is entropically driven by MC coming together to form hydrophobic interactions and water being liberated from interactions with MC. It is also well-known that the gelation temperature of MC can be reduced by the addition of salt. We have previously shown that the gelation temperature of MC can also be reduced by the addition of anionic polysaccharides, such as hyaluronan, which acts as a viscosity enhancer as well.

The specific use of hyaluronan (HA) and methylcellulose (MC), HAMC for the sustained release of sparingly soluble hydrophobic drugs is shown in this disclosure with nimodipine, a hydrophobic, sparingly-soluble vasodilator and calcium channel blocker used for treating central nervous system (CNS) disorders [A. Scriabine, T. Schuurman, J. Traber, *Pharmacological Basis for the Use of Nimodipine in Central Nervous*-System Disorders. Faseb J 3(7) (1989) 1799-1806; Y. S. R. Krishnaiah, P. Bhaskar, V. Satyanarayana, Penetration-enhancing effect of ethanol-water solvent system and ethanolic solution of carvone on transdermal permeability of nimodipine from HPMC gel across rat abdominal skin. *Pharmaceutical Development and Technology* 9(1) (2004) 63-74]. The incorporation of polymeric excipients into an injectable hydrogel (e.g., MC in the case of HAMC) has been found to increase the solubility of sparingly soluble drugs, such as nimodipine, and tune their rates of release. The rate of nimodipine dissolution in MC solution is slow, and depends on the initial drug particle size. Experimental and model analyses indicate that these differences in particle dissolution kinetics are reflected in the nimodipine release profiles from HAMC, and can be exploited in tailoring drug release rates. Thus based on these results, injectable hydrogel matrices can accelerate the delivery of sparingly soluble hydrophobic drugs, and can yield highly tunable release profiles that are dependent on how the drugs are introduced into the in situ gelling scaffold and on their particle sizes.

The data in the Examples presented herein indicate that the solubilization of the sparingly soluble hydrophobic pharmaceutical agent is mediated by the adsorption of MC to the hydrophobic drug particle. The adsorption is supported by (1) the steric stabilization of the drug particles observed in the presence of MC and not HA, and (2) the slow drug particle dissolution, which is more than 1000 times slower than it would be if it were controlled by solution- or gel-phase diffusion. The slow dissolution suggests that a particle-bound polymer layer is acting as a dissolution barrier. Once the drug is dissolved, it diffuses at a rapid rate that is characteristic of a small molecule rather than a micelle or molecular aggregate. This suggests that the increased solubility is not due to solubilization in micelle-like MC aggregates, but is rather caused by some interfacial interaction between the MC and the solid drug particle (i.e., adsorption of MC to the hydrophobic drug particle). Because MC adsorption is, at least in part likely driven by hydrophobic interactions—where hydrophobic segments of MC bind to the hydrophobic surface of the drug particle—this indicates that the solubilization effect can be extended to other hydrophobic drugs. The literature has relatively few reports of hydrophobic interactions, one example being Wen et al. "Hydrogen bonding interactions between adsorbed polymer molecules and crystal surface of acetaminophen", J. Colloid Interface Sci (2005) 325-335—that ascribe HPMC and PVP adsorption to drug particles to hydrogen bonding alone, and do not discuss the hydrophobic interactions at all.

More specifically, an injectable hydrogel matrix, comprised of hyaluronan and methylcellulose (HAMC), can be used for localized, sustained delivery of growth factors for treatment of spinal cord injury (SCI) and other injuries to the CNS such as traumatic brain injury and stroke. To better understand the ability of HAMC for the delivery of small molecules, the release of sparingly soluble neuroprotectant, nimodipine, was investigated experimentally and via continuum modeling. This revealed that the MC in HAMC increased the solubility of this sparingly soluble drug by over an order of magnitude, and enabled highly tunable release profiles to be achieved by varying the method by which the drug was introduced into the matrix.

When nimodipine was introduced into HAMC in solubilized form, it was rapidly released from the matrix within 8 hours. Conversely, when solid nimodipine particles were blended into HAMC in particulate form, the release rates were greatly reduced, giving rise to complete release over 2-3 days for small, sub-micron particles, and longer times for large, 100 µm particles. The nimodipine particle-loaded gels yielded particle size-dependent, biphasic release profiles, which reflected rapid release of the solubilized drug followed by the slow, dissolution-limited release of solid nimodipine. This demonstrates that injectable hydrogel matrices can act as polymeric excipients that accelerate the delivery of poorly soluble hydrophobic drugs and yield highly tunable release rates.

The anionic polysaccharide or a derivative thereof may comprise from about 100 to about 7,000 kg/mol and the methylcellulose or other water soluble hydrophobic cellulose derivative may comprise from about 2 to about 3,000 kg/mol. The ratio of anionic polysaccharide or a derivative thereof to the methylcellulose or other water soluble hydrophobic cellulose derivative may comprise from about 1:20 to about 1:1 w/w.

The amount of anionic polysaccharide or a derivative thereof may comprise from about 0.5% to about 5.0% by weight and the methylcellulose or other water soluble hydrophobic cellulose derivative may comprise from about 1.0% to about 20.0% by weight, more particularly, from about 5.0% to about 10% by weight of the matrix.

The dispersed hydrophobic therapeutic agent particles may be micro particles or nanoparticles. As used herein, "microparticles" refers to particles having a diameter of less than 1.0 mm, and more specifically between 1 and 1000 microns. Microparticles include microspheres, which are typically solid spherical microparticles. As used herein, "nanoparticles" refers to particles or structures in the nanometer range, typically from about 1 nm to about 1000 nm in diameter. The microparticles may be prepared in accordance with known methods, such as sonication as exemplified herein. The nanoparticles may be produced in accordance with suitable known methods as well. The selection of the size or sizes of the particles will determine the amount and rate of solubilisation that occurs, as well as the delivery profile for each sparingly soluble hydrophobic therapeutic agent present.

Given that the methyl cellulose or other cellulose derivative is hydrophobic and the pharmaceutical agent is selected from sparingly soluble hydrophobic drugs, the same solubilising effect will be found for any sparingly soluble hydrophobic therapeutic agent selected, and particularly for those that are specifically mentioned herein.

The delivered therapeutic agent load from the matrix may be in the range of from about 0.0001 to about 30 wt % (drug mass as a percentage of the matrix).

In the hydrogel matrix, the aqueous solution may be selected from the group comprising water, saline, artificial cerebrospinal fluid, and buffered solutions.

The hydrogel matrix components can be modified to alter the degradation rate of the hydrogel matrix and, hence, affect the rate of release of the pharmaceutical agent from the hydrogel matrix. One such modification involves addition of salts to alter the gelation temperature of the MC.

Another alternative to creating a more stable hydrogel matrix for slower degradation is to functionalize the polymers with thiol groups and acrylate groups. The hydrogel matrix is injected and gels quickly at the site of injection because, at physiological conditions, a Michael-type addition reaction occurs between the polymer end terminated with thiol and the polymer terminated with acrylate chains. This technique results in a product that is fast gelling with a high degree of gel strength, achieved as a result of linking multiple crosslinked polymers. For example, using a methacrylated polymer, such as methacrylated dextran, and a thiol conjugated polymer, such as PEG-dithiol or a peptide-dithiol, a crosslinked dextran gel can be achieved. Using a specific amino acid sequence that is enzymatically cleaved, a degradable, injectable crosslinked polysaccharide gel can be synthesized.

Another method of controlling degradation rates is to increase the hydrophobicity of the anionic polysaccharide, in particular the HA, which helps to maintain the integrity of gel through the formation of more hydrophobic junctions resulting in less water penetration. To render HA more hydrophobic, the reactive functional groups, hydroxyl or carboxyl, can be modified with hydrophobic molecules. For example, it is possible to modify the carboxyl group of HA with acetic hydrazide using standard coupling agents, such as carbodiimides like EDC. It should be noted that the carboxyl group is important for the highly viscous nature of the hydrogel matrix.

Another means to enhance sustained release of the pharmaceutical agent is to take advantage of ionic interactions between the therapeutic agent and the polymer. The highly negatively charged anionic gelling polymer engages in ionic interactions with positively charged molecules. Another alternative to further controlling drug release is by tethering or covalently bonding the pharmaceutical agent to the polymer. The agent releases from the hydrogel matrix upon breakage of the covalent bond or upon dissolution of the chain from the hydrogel matrix network. Methods of covalently bonding pharmaceutical agents to polymers may be employed that are known to those of skill in the art. Examples are described in Hoffman et al. [*Clinical Chemistry* 46(9): 1478-1486].

Chitosan, an amino-polysaccharide, is another example of a polymer which can be inverse thermal gelling polymer in a properly formulated hydrogel matrix. It is obtained by the alkaline deacetylation of chitin. Chitosan is both biocompatible and biodegradable and has inherent wound healing properties, in addition to a wide range of applications in drug delivery and tissue engineering. Chitin and chitosan are generally found as copolymers, and it is the chitin segments that are enzymatically degradable by lysozyme. It is a cationic polymer which is soluble in acidic conditions. Recently, Chenite et al. (*Biomaterials* 21:2155-2161, 2000) developed a thermogelling polymer by mixing beta-glycerophosphate (quadrature-GP) into a chitosan solution. Chitosan/beta-GP gels upon an increase in temperature where the gelation temperature is affected by both pH and beta-GP concentration. The negatively charged beta-GP molecules are attracted to the positively charged amine groups of chitosan, preventing chitosan from aggregating and precipitating at physiological pH. Upon an increase in temperature, a gel is formed because of the formation of physical junction zones which occur when hydrophobic and hydrogen bonding forces outweigh the interchain electrostatic repulsion forces.

The other hydrophobic water soluble cellulose derivatives may be selected from the group comprising hydroxypropyl methylcellulose, ethylcellulose, 3-O-ethylcellulose, hydroxypropyl methylcellulose phthalate, hydrophobically modified hydroxyethyl cellulose selected from ethyl(hydroxyethyl)cellulose, 6-O-alkylated cellulose, cellulose octanoate sulfate, cellulose lauroate sulfate, cellulose stearoate sulfate, and cationic derivatives thereof, 6-O-benzylcellulose, 2,3-di-O-methyl-6-O-benzylcellulose, 2,3-di-O— benzylcellulose, 2,3-di-O-benzyl-6-O-methylcellulose, 2,3,6-tri-O-benzylcellulose, hydroxypropyl methylcellulose acetate succinate, O-2-[2-(2-methoxyethoxy)ethoxy]acetyl cellulose.

The derivatives of hyaluronan may be esters of hyaluronan resulting from esterification with different classes of alcohols such as aliphatic, cycloaliphatic and heterocyclic.

The drug delivery hydrogel matrix of this invention has multiple applications and may be delivered via injection, transdermal, oral, sub-cutaneous, intranasal, vaginal, buccal, intrathecal, subdural, epidural, ocular space, dental, intratumoral, intramuscular, intraarticular, and intraveneously. The drug delivery synergistic hydrogel matrix is designed for delivery into a fluid-filled (or partially-filled) cavity. These include all cavities throughout the body, including but not limited to the intrathecal space, the intra-articular cavity, among others. The drug delivery system can also be injected into tissue.

While nimopidine has been used to illustrate the present disclosure, it should be understood that the at least one sparingly soluble hydrophobic therapeutic agent may be selected from any suitable sparingly soluble hydrophobic pharmaceutical agent or other type of agent for the non-pharmaceutical applications. The group of pharmaceutical agents is exemplified by the following: analgesics and anti-inflammatory agents: aloxiprin, auranofin, azapropazone, benorylate, diflunisal, etodolac, fenbufen, fenoprofen calcim, flurbiprofen, ibuprofen, indomethacin, ketoprofen, meclofenamic acid, mefenamic acid, nabumetone, naproxen, oxyphenbutazone, phenylbutazone, piroxicam, sulindac; anthelmintics: albendazole, bephenium hydroxynaphthoate, cambendazole, dichlorophen, ivermectin, mebendazole, oxamniquine, oxfendazole, oxantel embonate, praziquantel, pyrantel embonate, thiabendazole; anti-arrhythmic agents: amiodarone HCl, disopyramide, flecamide acetate, quinidine sulphate: anti-bacterial agents: benethamine penicillin, cinoxacin, ciprofloxacin HCl, clarithromycin, clofazimine, cloxacillin, demeclocycline, doxycycline, erythromycin, ethionamide, imipenem, nalidixic acid, nitrofurantoin, rifampicin, spiramycin, sulphabenzamide, sulphadoxine, sulphamerazine, sulphacetamide, sulphadiazine, sulphafurazole, sulphamethoxazole, sulphapyridine, tetracycline, trimethoprim; anti-coagulants: dicoumarol, dipyridamole, nicoumalone, phenindione; anti-depressants: amoxapine, maprotiline HCl, mianserin HCL, nortriptyline HCl, trazodone HCL, trimipramine maleate; anti-diabetics: acetohexamide, chlorpropamide, glibenclamide, gliclazide, glipizide, tolazamide, tolbutamide, anti-epileptics: beclamide, carbamazepine, clonazepam, ethotoin, methoin, methsuximide, methylphenobarbitone, oxcarbazepine, paramethadione, phenacemide, phenobarbitone, phenyloin, phensuximide, primidone, sulthiame, valproic acid; anti-fungal agents: amphotericin, butoconazole nitrate, clotrimazole, econazole nitrate, fluconazole, flucytosine, griseofulvin, itraconazole, ketoconazole, miconazole, natamycin, nystatin, sulconazole nitrate, terbinafine HCl, terconazole, tioconazole, undecenoic acid; anti-gout agents: allopurinol, probenecid, sulphin-pyrazone; anti-hypertensive agents: amlodipine, benidipine, darodipine, dilitazem HCl, diazoxide, felodipine, guanabenz acetate, isradipine, minoxidil, nicardipine HCl, nifedipine, nimodipine, phenoxybenzamine HCl, prazosin HCL, reserpine, terazosin HCL; anti-malarials: amodiaquine, chloroquine, chlorproguanil HCl, halofantrine HCl, mefloquine HCl, proguanil HCl, pyrimethamine, quinine sulphate; anti-migraine agents: dihydroergotamine mesylate, ergotamine tartrate, methysergide maleate, pizotifen maleate, sumatriptan succinate; anti-muscarinic agents: atropine, benzhexyl HCl, biperiden, ethopropazine HCl, hyoscyamine, mepenzolate bromide, oxyphencylcimine HCl, tropicamide; anti-neoplastic agents and Immunosuppressants: aminoglutethimide, amsacrine, azathioprine, busulphan, chlorambucil, cyclosporin, dacarbazine, estramustine, etoposide, lomustine, melphalan, mercaptopurine, methotrexate, mitomycin, mitotane, mitozantrone, procarbazine HCl, tamoxifen citrate, testolactone; anti-protazoal agents: benznidazole, clioquinol, decoquinate, diiodohydroxyquinoline, diloxanide furoate, dinitolmide, furzolidone, metronidazole, nimorazole, nitrofurazone, ornidazole, tinidazole; anti-thyroid agents: carbimazole, propylthiouracil; anxiolytic, sedatives, hypnotics and neuroleptics: alprazolam, amylobarbitone, barbitone, bentazepam, bromazepam, bromperidol, brotizolam, butobarbitone, carbromal, chlordiazepoxide, chlormethiazole, chlorpromazine, clobazam, clotiazepam, clozapine, diazepam, droperidol, ethinamate, flunanisone, flunitrazepam, fluopromazine, flupenthixol decanoate, fluphenazine decanoate, flurazepam, haloperidol, lorazepam, lormetazepam, medazepam, meprobamate, methaqualone, midazolam, nitrazepam, oxazepam, pentobarbitone, perphenazine pimozide, prochlorperazine, sulpiride, temazepam, thioridazine, triazolam, zopiclone; beta-blockers, acebutolol, alprenolol, atenolol, labetalol, metoprolol, nadolol, oxprenolol, pindolol, propranolol; cardiac inotropic agents: amrinone, digitoxin, digoxin, enoximone, lanatoside C, medigoxin; corticosteroids: beclomethasone, betamethasone, budesonide, cortisone acetate, desoxymethasone, dexamethasone, fludrocortisone acetate, flunisolide, flucortolone, fluticasone propionate, hydrocortisone, methylprednisolone, prednisolone, prednisone, triamcinolone; diuretics: acetazolamide, amiloride, bendrofluazide, bumetanide, chlorothiazide, chlorthalidone, ethacrynic acid, frusemide, metolazone, spironolactone, triamterene; anti-parkinsonian agents: bromocriptine mesylate, lysuride maleate; gastro-intestinal agents: bisacodyl, cimetidine, cisapride, diphenoxylate HCl, domperidone, famotidine, loperamide, mesalazine, nizatidine, omeprazole, ondansetron HCL, ranitidine HCl, sulphasalazine; histamine H; receptor antagonists: acrivastine, astemizole, cinnarizine, cyclizine, cyproheptadine HCl, dimenhydrinate, flunarizine HCl, loratadine, meclozine HCl, oxatomide, terfenadine; lipid regulating agents: bezafibrate, clofibrate, fenofibrate, gemfibrozil, probucol; nitrates and other anti-anginal agents: amyl nitrate, glyceryl trinitrate, isosorbide dinitrate, isosorbide mononitrate, pentaerythritol tetranitrate; nutritional agents: betacarotene, vitamin A, vitamin B2, vitamin D, vitamin E, vitamin K; opioid analgesics: codeine, dextropropoxyphene, diamorphine, dihydrocodeine, meptazinol, methadone, morphine, nalbuphine, pentazocine; sex hormones; clomiphene citrate, danazol, ethinyl estradiol, medroxyprogesterone acetate, mestranol, methyltestosterone, norethisterone, norgestrel, estradiol, conjugated oestrogens, progesterone, stanozolol, stibestrol, testosterone, tibolone; stimulants: amphetamine, dexamphetamine, dexfenfluramine, fenfluramine, mazindol; and mixtures of hydrophobic drugs may, of course, be used where therapeutically effective.

Examples of sparingly soluble hydrophobic molecules that may be used for food formulations include, but are not limited to hydrophobic neutracueticals, examples of which include flavonoids, isoflavones, and theobromine; hydrophobic vitamins, examples of which are Vitamin A (retinol, retinoids and carotenoids), Vitamin D (ergocalciferol and cholecalciferol), Vitamin E (tocopherol and tocotrienol) and Vitamin K (phylloquinone and menaquinone).

Examples of cosmetic agents that may be included in the hydrogel matrices include a variety of cosmetic additives that fall in the category of sparingly soluble hydrophobic agents, examples of which include but are not limited to fragrances, examples of which are dihydromyrcenol, limonene, benzyl acetate, Romascone; antibacterial agents, examples of which are chlorhexidine, triclosan; and for skin therapy, examples are some cosmetic applications also use vitamins and nutraceuticals listed above.

When more than one pharmaceutical agent or other agent is present, each will have its own release profile which will be determined by its solubilisation in the methyl cellulose or other water soluble cellulose derivative and its particle size or sizes. A mixture of particle sizes may also be selected to provide a more tailored release rate.

The specific use of hyaluronan (HA) and methylcellulose (MC), (HAMC) for the sustained release of low molecular weight drugs is exemplified in this disclosure with nimodipine, a hydrophobic, sparingly-soluble vasodilator and calcium channel blocker used for treating central nervous system (CNS) disorders [A. Scriabine, T. Schuurman, J. Traber, *Pharmacological Basis for the Use of Nimodipine in Central Nervous-System Disorders*. Faseb J 3(7) (1989) 1799-1806; Y. S. R. Krishnaiah, P. Bhaskar, V. Satyanarayana, Penetration- enhancing effect of ethanol-water solvent system and ethanolic solution of carvone on transdermal permeability of nimodipine from HPMC gel across rat abdominal skin. *Pharmaceutical Development and Technology* 9(1) (2004) 63-74]. The incorporation of polymeric excipients into an injectable hydrogel (e.g., MC in the case of HAMC) has been found to increase the solubility of sparingly soluble drugs, such as nimodipine, and tune their rate of release. The rate of nimodipine dissolution in MC solution is slow, and depends on the initial drug particle size. Experimental and model analyses indicate that these differences in particle dissolution kinetics are reflected in the nimodipine release profiles from HAMC, and can be exploited in tailoring drug release rates.

Thus based on these results, injectable hydrogel matrices can accelerate the delivery of hydrophobic, sparingly soluble drugs, or any food or cosmetic sparingly soluble hydrophobic agent and can yield highly tunable release profiles that are dependent on how the drug or agent is introduced into the in situ gelling scaffold.

An injectable hydrogel, comprised of hyaluronan and methylcellulose (HAMC), shows promise for localized, sustained delivery of growth factors for treatment of spinal cord injury (SCI). To better understand its potential for the delivery of small molecules, the release of sparingly soluble neuroprotectant, nimodipine, was investigated experimentally and via continuum modeling. This revealed that the MC in HAMC increased the solubility of this sparingly soluble drug by over an order of magnitude, and enabled highly tunable release profiles to be achieved by varying the method by which the drug was introduced into the matrix.

When nimodipine was introduced into HAMC in solubilized form, it was rapidly released from the scaffold within 8 hours. Conversely, when solid nimodipine particles were blended into HAMC in particulate form, the release rates were greatly reduced, giving rise to complete release over 2-3 days for small, sub-micron particles, and longer times for large, 100 μm particles. The nimodipine particle-loaded gels yielded particle size-dependent, biphasic release profiles, which reflected rapid release of the solubilized drug followed by the slow, dissolution-limited release of solid nimodipine. This indicates that injectable hydrogel matrices can act as polymeric excipients that accelerate the delivery of poorly soluble drugs and yield highly tunable release rates.

EXAMPLES

To prepare nimodipine (Sigma Aldrich, Oakville, ON, Canada) for the release study, two types of nimodipine formulations were prepared at room temperature: (1) 0.5 mg/ml of nimodipine particles dissolved in 20 v/v % ethanol in water; and (2) 0.5 mg/ml of nimodipine particles dispersed in a 0.1 wt % methylcellulose (MC, Sigma Aldrich) solution in artificial CSF (aCSF). To vary the drug particle size, the particulate dispersions were either used as received (non-sonicated particles); or sonicated to reduce particle size for 1 or 5 min at 20 kHz, 40% amplitude, using a Sonics Vibra Cell CV18™ tip sonicator (Sonics & Materials Inc., Newtown, Conn., USA). The nimodipine particles dispersed in MC were sized via dynamic light scattering (DLS, Malvern Zetasizer Nano ZS™, Worcestershire, UK) for the sonicated sub-micron particles, and laser diffraction (Malvern Mastersizer 2000™, Worcestershire, UK) for the non-sonicated particles.

The particle dispersions were left for 3 days at room temperature to ensure that particles were stable in dispersion before incorporation into HAMC.

Incorporation of Nimodipine in HAMC

Thermogelling, sterile-filtered HAMC blends were prepared as previously described [D. Gupta, C. H. Tator, M. S. Shoichet, Fast- gelling injectable blend of hyaluronan and methylcellulose for intrathecal, localized delivery to the injured spinal cord. *Biomaterials* 27(11) (2006) 2370-2379] by dissolving hyaluronan (HA, Novamatrix™, Sandvika, Norway) at 2 wt % into MC at 7 wt %. For nimodipine release studies, 100 μl of nimodipine formulations was added to 900 μl of MC dissolved in aCSF, yielding a 7 wt % MC/nimodipine dispersion, with a nimodipine concentration of 50 mg/ml. HA was then dissolved into the MC/nimodipine dispersion at 2 wt %. The HAMC solution was then vortexed (Vortex-Genie 2™, 120V, 60 Hz 0.65 amps, Scientific Industries Inc., New York, N.Y., USA) until a clear, homogeneous, highly-viscous solution was obtained [D. Gupta, C. H. Tator, M. S. Shoichet, Fast-gelling injectable blend of hyaluronan and methylcellulose for intrathecal, localized delivery to the injured spinal cord. *Biomaterials* 27(11) (2006) 2370-2379].

Nimodipine Dissolution Kinetics

To determine the effect of MC and HA on nimodipine dissolution in HAMC, 0.5 mg/ml nimodipine dispersions (composed of either non-sonicated larger particles or 1 or 5 minute sonicated sub-micron particles) was dispersed in 10 ml of either 7 wt % MC or 0.25 wt % HA in aCSF. Here, the HA solution composition was adjusted to match the viscosity of the 7 wt % MC (ca. 0.5 Pa·s), to maintain similar hydrodynamic conditions and mass transfer coefficients between the two receiving mediums. The dispersions were allowed to dissolve at 25° C. under constant stirring. The concentration of solubilized nimodipine was tracked over a 9 day period using the NanoDrop™ Spectrophotometer ND-100™ (Wilmington, Del., USA, λ=275 nm, extinction coefficient=4.217 ml mg$^{-1}$ cm$^{-1}$).

Drug Release Studies

One hundred microliters of HAMC containing nimodipine was injected onto the bottom of a 2 ml eppendorf tube containing 900 μl of aCSF at 37° C. [D. Gupta, C. H. Tator, M. S. Shoichet, Fast-gelling injectable blend of hyaluronan and methylcellulose for intrathecal, localized delivery to the injured spinal cord. *Biomaterials* 27(11) (2006) 2370-2379], thereby mimicking the 10% volume dilution expected in the intrathecal space of a rat animal model. At various time points, the supernatant was removed and replaced with the same volume of fresh aCSF. To determine the amount of drug released between each time point, the absorbance of supernatant containing released nimodipine was measured using the NanoDrop™ Spectrophotometer.

Nimodipine Dissolution Kinetics

Figure 1:
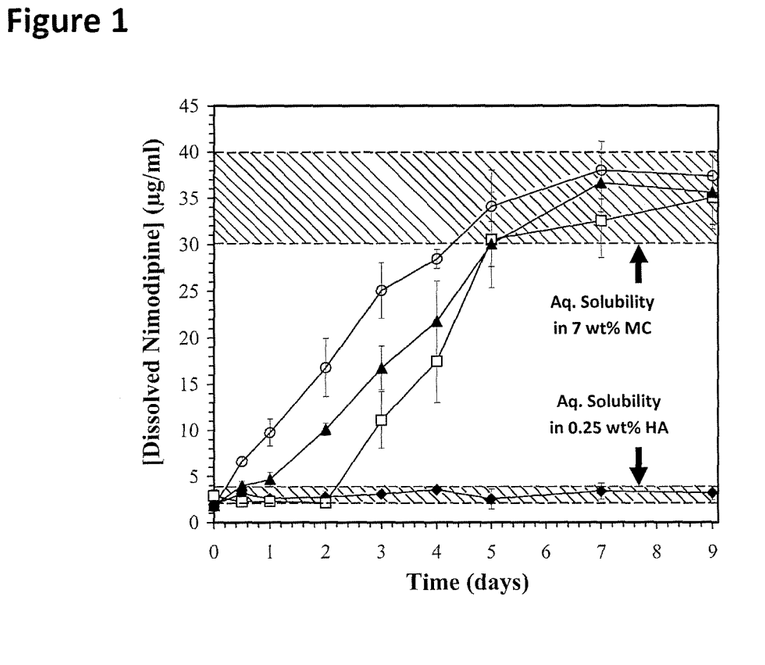
FIG. 1 illustrates a comparison of nimodipine solubility in MC and HA, with different nimodipine particle sizes: (♦) 100-□m nimodipine particles in 0.25 wt % HA; and (□) 100-μm, (▲) 900-nm, and (○) 380-nm nimodipine particles in 7 wt % MC. The upper shaded concentration range indicates nimodipine solubility values achieved in 7 wt % MC, while the lower shaded range indicates aqueous nimodipine solubility reported in the literature [A. Yoshida, M. Yamamoto, T. Itoh, T. Irie, F. Hirayama, K. Uekama, Utility of 2-Hydroxypropyl-Beta-Cyclodextrin in an Intramuscular Injectable Preparation of Nimodipine. *Chemical & Pharmaceutical Bulletin* 38(1) (1990) 176-179]. Nimodipine Preparation.

The particle size and the properties of the dissolution medium are expected to influence the dissolution kinetics and release profiles of nimodipine. To investigate the effects of particle size and the presence of MC and HA on the solubilization of nimodipine, the dissolution of three polydisperse populations of nimodipine particles with diameters of 100±30 μm, 900±60 nm (second order polydispersity factor, PI=0.48), and 380±20 nm (PI=0.64), as sized by laser diffraction and DLS, were quantified over time in well-stirred MC and HA solutions. To ensure that the liquid phase mass transfer coefficients would be similar for the two polymer solutions, the viscosity of the HA solution was matched to that of 7 wt % MC, resulting in an HA concentration of 0.25 wt %. FIG. 1 shows that the concentration of nimodipine ultimately solubilized in 7 wt % reached a plateau at approximately 30-40 μg/ml, which may be interpreted as its solubility limit. This solubility is an order of magnitude higher than nimodipine's literature aqueous solubility of 2-4 μg/ml [A. Yoshida, M. Yamamoto, T. Itoh, T. Irie, F. Hirayama, K. Uekama, Utility of 2-Hydroxypropyl-Beta-Cyclodextrin in an Intramuscular Injectable Preparation of Nimodipine. Chemical & Pharmaceutical Bulletin 38(1) (1990) 176-179], which was also observed in 0.25 wt % HA. In contrast to previous work where polymeric excipients prevented crystallization of supersaturated drug solutions over time [Y. S. R. Krishnaiah, P. Bhaskar, V. Satyanarayana, Penetration-enhancing effect of ethanol-water solvent system and ethanolic solution of carvone on transdermal permeability of nimodipine from HPMC gel across rat abdominal skin. *Pharmaceutical Development and Technology* 9(1) (2004) 63-74; S. L. Raghavan, K. Schuessel, A. Davis, J. Hadgraft, Formation and stabilisation of triclosan colloidal suspensions using supersaturated systems. *Int J Pharm* 261(1-2) (2003) 153-158], here the addition of MC leads to amplified drug solubilization. Conversely, the presence of HA had no measurable impact on nimodipine solubility.

The dissolution of each particle type in 7 wt % MC appeared to occur in two stages. The first stage corresponded to the solubility of nimodipine in water (2-4 μg/ml) and occurred within minutes, whereas the second stage corresponded to its solubility in MC (30-40 μg/ml) and occurred within several days. Interestingly, the larger 100-μm (and to a lesser extent the 900-nm) nimodipine particles showed an induction period in their dissolution profiles in MC, where the enhanced solubilization mediated by MC was not observed until 1-3 days into the dissolution process. The induction time increased with particle size. For all nimodipine particles studied, the plateau of solubilized drug was attained after approximately 1 week in MC solution.

Visual observation of the nimodipine particles revealed that MC also affects their dispersion properties. All three particles formed large ~O(1000 μm) aggregates in HA, and smaller ~O(10 μm) aggregates in MC (data not shown). This indicates that when dispersed in MC solution the large, 100-μm particles fragment and dissolve, while the small, sub-micron particles undergo some aggregation. The improved colloidal stability that is mediated by MC suggests that MC adsorbs to the surface of the nimodipine particles and prevents flocculation of nimodipine into larger particles through steric stabilization. This improved colloidal stability is consistent with the polymer-mediated stabilization reported for colloidal drug dispersions in aqueous hydroxypropyl methylcellulose solutions [S. L. Raghavan, K. Schuessel, A. Davis, J. Hadgraft, Formation and stabilisation of triclosan colloidal suspensions using supersaturated systems. *Int J Pharm* 261 (1-2) (2003) 153-158].

To further probe the mechanism of nimodipine dissolution in the presence of MC, the mass transfer coefficient, $k_m$, for the slower second stage of particle dissolution in MC was estimated via [Bird RB. Stewart WE, Lightfoot EN, *Transport Phenomena*, John Wiley and Sons, 2006]:

$$\frac{dC_A}{dt} \sim \frac{k_m a}{V} C_A^{Sat} \qquad (1)$$

where a is the total surface area of the 10-μm nimodipine particle flocs, V is the volume of the receiving MC solution, $C_A^{sat}$ is the saturation concentration of nimodipine in 7 wt % MC, and $dC_A/dt$ is the approximate slope of the dissolution curves estimated to be ~O(10μg/ml·day) from FIG. 1. This analysis yields a mass transfer coefficient of $k_m \sim O(10^{-6}$ cm/s), which is more than three orders of magnitude lower than the minimum mass transfer coefficient predicted for solution mass transfer-controlled dissolution. The $k_m$ for solution mass transfer-controlled dissolution is $\sim 2 \times 10^{-3}$ cm/s, estimated for the 10- μm nimodipine aggregates in the absence of convection, where the Sherwood number (Sh) is equal to two [Tosun. I., *Modeling in Transport Phenomena, a Conceptual Approach*, 2nd ed., Elsevier, 2007]: $Sh = k_m d_p / D_A$, where $d_p$ is the drug particle diameter, and $D_A$ is the molecular diffusivity of the drug. This suggests that the solubilization of nimodipine is not limited by the solution mass transfer of nimodipine, but is rather governed by another slower process. A layer of adsorbed polymer may be slowing down the dissolution of nimodipine particles. The hypothesis that adsorption of MC improves drug solubility is supported by following: (1) the steric stabilization of the nimodipine particles observed in the presence of MC; and (2) the high diffusivity of nimodipine observed in HAMC ($D_A \sim O(10^{-5}$ cm²/s), see Section 3.2.1.). This high $D_A$ value is characteristic of small molecule diffusion, suggesting that once the nimodipine is solubilized in HAMC, it remains in a molecular state. Importantly, while the presence of MC retards the rate of drug particle dissolution, the solubility is enhanced. Thus, the increased amount of solubilized drug at the beginning of the release process (e.g., from <4 to <40 μg/ml nimodipine) should accelerate the rate of drug release when MC is present. From these results, the slow, particle size-dependent process of MC-mediated drug dissolution was expected to enable tunable acceleration of hydrophobic drug release from HAMC (and other similar injectable gels) by modulating the drug fraction that is solubilized at the beginning of the release profile. This can be achieved by either varying the size of the drug particles that are used in the hydrogel preparation or the time period between the preparation and application of the HAMC blend.

Nimodipine Release from HAMC
Release of Solubilized Nimodipine

Figure 2:
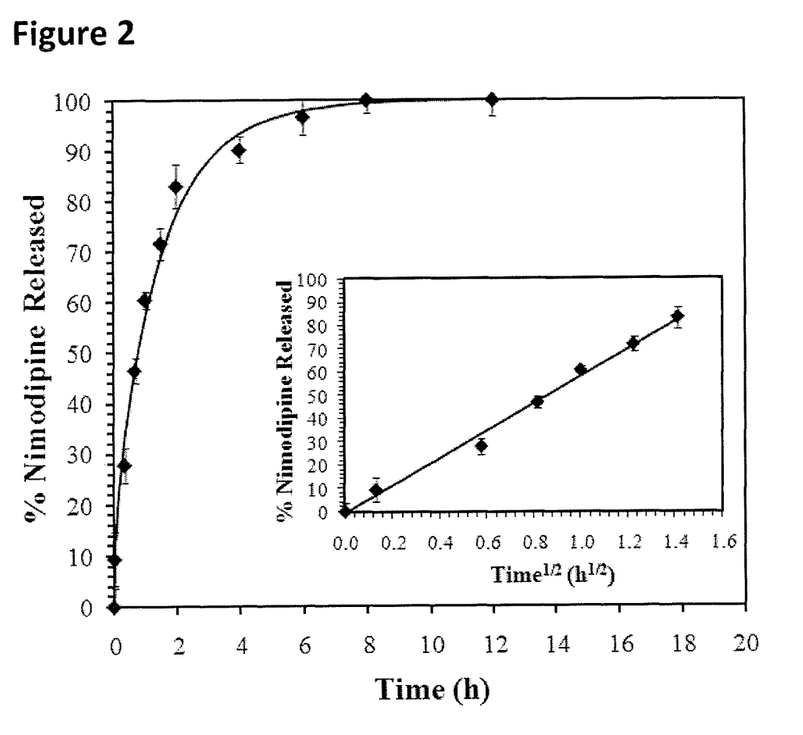
FIG. 2 illustrates release of solubilized nimodipine plotted against time (mean±standard deviation, n=3). The curve represents the model fit (Eq. 3b) for the release data. The inset shows that the drug release scales linearly with the square root of time, according to Eq. 2, for the first 70-80% of released nimodipine.

HAMC may be classified as a matrix drug delivery system where nimodipine is distributed throughout the gel network [B. N. Nalluri, C. Milligan, J. H. Chen, P. A. Crooks, A. L. Stinchcomb, In vitro release studies on matrix type transdermal drug delivery system of naltrexone and its acetyl prodrug. *Drug Dev Ind Pharm* 31(9) (2005) 871-877; C. C. Lin, A. T. Metters, Hydrogels in controlled release formulations: Network design and mathematical modeling. *Adv Drug Deliver Rev* 58(12-13) (2006) 1379-1408]. Solubilized nimodipine, which was predissolved in ethanol to produce a 50 μg/ml nimodipine and 2% v/v ethanol solution in HAMC, was fully released within 8 h (FIG. 2). The square root scaling of the release profile (see FIG. 2 inset) suggests that it is diffusion-controlled. For a planar geometry, such as the release of nimodipine from the top of a cylindrical HAMC gel, drug release can be estimated by the analytical approximation [C. S. Brazel, N. A. Peppas, Modeling of drug release from swellable polymers. *Eur J Pharm Biopharm* 49(1) (2000) 47-58]:

$$\frac{M_t}{M_\infty} = \frac{2}{L} \sqrt{\frac{D_A}{\pi}} \cdot t^{0.5} \qquad (2)$$

where $M_t/M_\infty$ is the fraction of drug molecules released from the hydrogel at time t, $D_A$ is the diffusivity of the drug in the matrix, and L is the scaffold thickness [C. S. Brazel, N. A. Peppas, Modeling of drug release from swellable polymers. *Eur J Pharm Biopharm* 49(1) (2000) 47-58]. For an estimated gel thickness of 0.37 cm, the fitted diffusivity value of $1.0 \times 10^{-5}$ cm²/s is characteristic of the diffusion of small molecules and suggests that the drug remains dissolved during the release process. The proportionality to the square root of time is maintained for the first 70-80% of release [C. C. Lin, A. T. Metters, Hydrogels in controlled release formulations: Network design and mathematical modeling. *Adv Drug Deliver Rev* 58(12-13) (2006) 1379-1408; J. Siepmann, N. A. Peppas, Modeling of drug release from delivery systems based on hydroxypropyl methylcellulose (HPMC). *Adv Drug Deliver Rev* 48(2-3) (2001) 139-157], after which drug depletion affects the concentration gradient, thus reducing the driving force for drug release. This also supports our previous findings that diffusion is the dominant mechanism of drug release from HAMC [Y. S. R. Krishnaiah, P. Bhaskar, V. Satyanarayana, Penetration-enhancing effect of ethanol -water solvent system and ethanolic solution of carvone on transdermal permeability of nimodipine from HPMC gel across rat abdominal skin. *Pharmaceutical Development and Technology* 9(1) (2004) 63-74].

Release of Particulate Nimodipine

Figure 3:
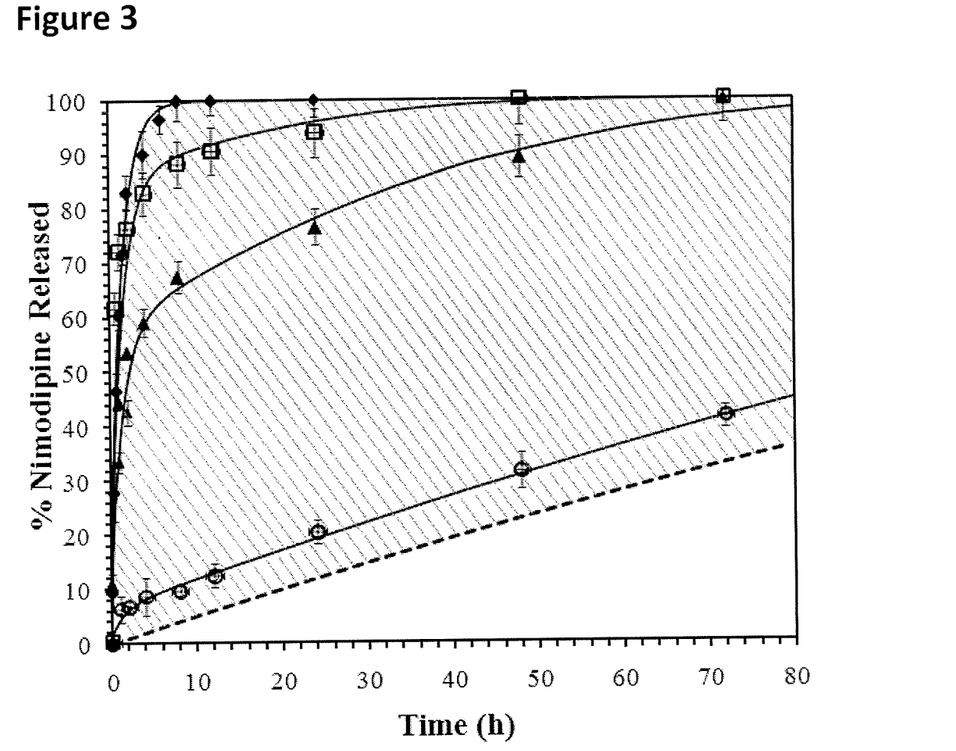
FIG. 3 illustrates a comparison of model predictions to experimental data for: (♦) solubilized nimodipine, (□) 380 nm particulate nimodipine, (▲) 900 nm particulate nimodipine, (○) 100 μm particulate nimodipine (mean±standard deviation, n=3). The solid lines (-) depict the model predictions, the dashed line (- - -) represents the slowest release predicted by Eq. 6, and the shaded region indicates the range of release profiles obtained by varying the formulation of nimodipine. This range is bounded by the Fickian model (upper limit) and that described by Eq. 6 (lower limit).

When nimodipine was introduced in particulate form, its release from HAMC was significantly slower than the soluble form. The complete release of 380 nm and 900 nm nimodipine particle formulations from HAMC was achieved at 48 h and 72 h, respectively (FIG. 3). For 100 μm nimodipine particles, only ~40% of the drug was released from HAMC after 3 days, likely because only a fraction of the total nimodipine is soluble and able to diffuse from the gel at a given time.

The release profiles obtained using gels loaded with nimodipine particles were biphasic. Submicron particles yielded a high initial burst release (ca. 80% for the 380 nm particles, and ca. 60% for the 900 nm particles), occurring within the first few hours, similar to that of the release of solubilized nimodipine. This initial burst release phase was followed by a second slower release phase, which takes place over 2-3 days. These two phases correspond to the rapid release of the drug that is solubilized at the beginning of the release process followed by slower dissolution-limited release of the drug that remains in particulate form. Likewise, the 100-μm particles yielded a 5-10% burst release followed by the slow dissolution-controlled release. This burst release is consistent with the slower solubilization rates of larger nimodipine particles in MC solution, and indicates that the release profiles can be tuned over a wide range of release rates by varying the method by which sparingly soluble drug is introduced into the gel.

Model Analysis of the Release Profiles

To analyze the release of nimodipine from HAMC, a generalized model was developed based on diffusion- and particle dissolution-controlled mass transport. It was assumed that the nimodipine particles were uniformly distributed within HAMC, and that the solubilized drug concentration and the radii of the dissolving drug particles varied with respect to both time and spatial position within the gel. Using these assumptions, the temporal variation in drug particle size and solubilized drug concentrations can be estimated using two coupled differential equations:

$$\frac{dR_1}{dt} = -k_m \frac{MW_A}{\rho_A}(C_A^{Sat} - C_A) \qquad (3a)$$

-continued $$\frac{\partial C_A}{\partial t} = D_A \frac{\partial^2 C_A}{\partial z^2} + 4\pi k_m R_1^2 n_p (C_A^{Sat} - C_A) \quad (3b)$$

Here, $C_A$ is the drug concentration at specific spatial (z) and temporal (t) points within the matrix, $C_A^{Sat}$ is the saturation concentration of the drug in the gel, and $n_p$ is the number of particles per unit volume within the matrix (number of particles/cm$^3$), $MW_A$ is the molecular weight of the drug, and $\rho_A$ is the density of the drug particle. $D_A$ is the diffusivity of drug molecules in the hydrogel matrix, and $k_m$ is the mass transfer coefficient for drug particle dissolution. $R_1$ is the drug particle radius, which varies with respect to time, t and position, z. $R_1$ is a function of drug particle position within the gel because dissolution is driven by the concentration gradient of dissolved molecules around the particle. For regions closer to the surface of the gel, the drug diffuses out more quickly compared to the interior regions of the gel, leading to faster particle dissolution. Equation 3a describes the dissolution of the drug particles over time [N. A. Peppas, A Model of Dissolution -Controlled Solute Release from Porous Drug Delivery Polymeric Systems. *Journal of Biomedical Materials Research* 17(6) (1983) 1079-1087; M. I. Cabrera, J. A. Luna, R. J. A. Grau, Modeling of dissolution -diffusion controlled drug release from planar polymeric systems with finite dissolution rate and arbitrary drug loading. *Journal of Membrane Science* 280(1-2) (2006) 693-704]. Likewise, Equation 3b provides a microscopic materials balance on the solubilized drug in the gel matrix, where the change in the local solubilized drug concentration reflects the balance between the dissolution of the drug particles and the diffusion of the drug out of the gel. Using the appropriate boundary conditions, where flux at the inner boundary and the drug concentration at the outer boundary are both equal to zero, this system of equations was solved numerically with MATLAB™ via finite difference approximation. Using the $D_A$-value fitted to Equation 2 in Section 3.2.1 (1.0×10$^{-5}$ cm$^2$/s) and an approximate $C_A^{sat}$-value of 40 µg/ml and initial particle diameter of 10 µm, the numerical solutions given in terms of $C_A(z,t)$ and $R_1(t,z)$ (not shown) were obtained. These profiles were then integrated over the volume of the scaffold to generate the release curves showing the amount of drug released over time. The model release curves were fitted to the experimental release profiles by varying the fraction of the drug that was dissolved at the beginning of the release experiment ($f_{dissolved}$, which affects the initial solubilized drug concentration and the drug particle radius at the start of the experiment) and $k_m$ (see Table 1).

TABLE 1

Model parameters used for fitting Equations 3a and 3b to the experimental data

| Formulation | $D_A$ (cm$^2$/s) | $C_A^{Sat}$ (µg/ml) | $f_{dissolved}$ | $k_m$ (cm/s) |
|---|---|---|---|---|
| Solubilized nimodipine | 1.0 × 10$^{-5}$ | 40 | 1.00 | N/A |
| 380 nm nimodipine particles | 1.0 × 10$^{-5}$ | 40 | 0.85 | 2.5 × 10$^{-5}$ |
| 900 nm nimodipine particles | 1.0 × 10$^{-5}$ | 40 | 0.62 | 2.3 × 10$^{-5}$ |
| 100 µm nimodipine particles | 1.0 × 10$^{-5}$ | 40 | 0.06 | 7.5 × 10$^{-6}$ |

The model fits were in excellent agreement (see FIG. 3) with all four experimental release profiles. Although there was some uncertainty in the initial particle size and, to a lesser extent, $C_A^{sat}$, the models support the interpretation of the biphasic release mechanism. They revealed consistent $k_m$-values on the order of 10$^{-5}$ cm/s and $f_{dissolved}$ values that varied from 6% for the 100 µm particles, to 62% for the 380 nm and 85% for the 900 nm particles, to 100% for the solubilized nimodipine. This suggests that a full range of $f_{dissolved}$-values can be achieved by varying the way in which the drug is introduced into HAMC.

Given the broad range of release profiles that can be achieved using HAMC, it is useful to define "limiting" analytical expressions for the fastest and slowest possible release profiles. The fastest possible release occurs when the entire amount of drug is dissolved, as in the case of the solubilized nimodipine, where the release profile can be estimated using Equation 2. Conversely, the release profile is slowest when all loaded drug starts out in the particulate state (i.e., $f_{dissolved}$=0.00). A simple analytical expression for the release profile in this situation can be obtained under two sets of circumstances: (1) the release rate is controlled only by diffusion through the gel matrix, where drug particle dissolution is faster than the diffusion of the drug out of the gel, or (2) the release rate is controlled only by the dissolution of the drug particle, where the diffusion of the drug out of the gel is faster than the drug particle dissolution. The time scales of these two processes can be compared by defining a dimensionless number ($\xi$) that represents the ratio between the characteristic times of drug diffusion out of the gel and drug particle dissolution:

$$\xi = \frac{k_m n_p R_1^2 L^2}{D_A} \quad (4)$$

When $\xi \gg 1$, the release profile is governed exclusively by the diffusion of the drug through the aqueous gel matrix, and the release profile can be described by the Higuchi shrinking core model [W. I. Higuchi, Diffusional Models Useful in Biopharmaceutics -Drug Release Rate Processes. *J Pharm Sci* 56(3) (1967) 315-324]:

$$\frac{M_t}{M_\infty} = \sqrt{\frac{D_A}{L^2}\left[\frac{3C_A^{Sat}MW_A}{2\pi R_{1,0}^3 \rho_A n_p} - \left(\frac{3C_A^{Sat}MW_A}{4\pi R_{1,0}^3 \rho_A n_p}\right)^2\right]} \cdot t^{0.5} \quad (5)$$

Conversely, when $\xi \ll 1$, release is governed exclusively by slow dissolution of the drug particles. The release of the particulate nimodipine from HAMC ($\xi \sim O(10^{-2}\text{-}10^{-3})$) exemplifies this situation, and enables the determination of a limiting release profile equation through the solution of Equation 3a. In this case, since the diffusion of the drug out of the gel is rapid relative to the particle dissolution rate, it is reasonable to assume that $C_A$ is negligible relative to $C_A^{sat}$. This decouples Equation 3a from Equation 3b, and enables the analytical solution for $R_1(t)$, yielding:

$$\frac{M_t}{M_\infty} = 1 - \left(1 - \frac{k_m MW_A C_A^{Sat}}{\rho_A R_{1,0}}t\right)^3 \quad (6)$$

which is the scaling predicted by the Hixson-Crowell model [A. W. Hixson, J. H. Crowell, Dependence of reaction velocity upon surface and agitation I-*Theoretical consideration*. *Industrial and Engineering Chemistry* 23 (1931) 923-931].

Assuming the $k_m$-value that was fitted in the case of the 100 μm particles, which is the closest condition to the limit that was tested, Equation 6 predicts a limiting release profile (dashed lines in FIG. 3) that is similar to the experimental profile obtained for the large nimodipine particles, but has a starting point at the origin.

As can be seen from the shaded region of FIG. 3, by varying the method by which the nimodipine is introduced into HAMC a broad range of release profiles can be achieved. These are bounded by the Fickian release obtained in the case of the fully-solubilized nimodipine and the nearly linear release that is predicted by Equation 6. Significantly, under each condition described above, the drug release rate increases with increasing $C_A^{Sat}$, as indicated by Eq. 3a, 3b, 5, and 6.

HAMC as a Delivery Platform for Hydrophobic Drugs

It has been shown that the incorporation of polymeric excipients as structural elements of an injectable hydrogel, such as MC in the case of HAMC, can increase the aqueous solubility of hydrophobic drugs. Unlike previous work where polymer additives reduced the rate of drug crystallization [Y. S. R. Krishnaiah, P. Bhaskar, V. Satyanarayana, Penetration-enhancing effect of ethanol-water solvent system and ethanolic solution of carvone on transdermal permeability of nimodipine from HPMC gel across rat abdominal skin. *Pharmaceutical Development and Technology* 9(1) (2004) 63-74; L. Zema, A. Maronii, A. Foppoli, L. Palugan, M. E. Sangalli, A. Gazzaniga, Different HPMC viscosity grades as coating agents for an oral time and/or site- controlled delivery system: An investigation into the mechanisms governing drug release. *J Pharm Sci* 96(6) (2007) 1527-1536; S. L. Raghavan, A. Trividic, A. F. Davis, J. Hadgraft, Effect of cellulose polymers on supersaturation and in vitro membrane transport of hydrocortisone acetate. *Int J Pharm* 193(2) (2000) 231-237; K. Yamashita, T. Nakate, K. Okimoto, A. Ohike, Y. Tokunaga, R. Ibuki, K. Higaki, T. Kimura, Establishment of new preparation method for solid dispersion formulation of tacrolimus. *Int J Pharm* 267(1-2) (2003) 79-91; S. L. Raghavan, K. Schuessel, A. Davis, J. Hadgraft, Formation and stabilisation of triclosan colloidal suspensions using supersaturated systems. *Int J Pharm* 261(1-2) (2003) 153-158; U. Kumprakob, J. Kawakami, I. Adachi, Permeation enhancement of ketoprofen using a supersaturated system with antinucleant polymers. Biological & *Pharmaceutical Bulletin* 28(9) (2005) 1684-1688; X. G. Ma, J. Taw, C. M. Chiang, Control of drug crystallization in transdermal matrix system. *Int J Pharm* 142(1) (1996) 115-119; P. N. Kotiyan, P. R. Vavia, Eudragits: Role as crystallization inhibitors in drug-in-adhesive transdermal systems of estradiol. *Eur J Pharm Biopharm* 52(2) (2001) 173-180], the presence of 7 wt % MC in aqueous solution gives rise to a tenfold amplification in nimodipine solubility. This increase in drug solubility significantly accelerates drug release from the hydrogel, and suggests that injectable hydrogel matrices can act as polymeric excipients that accelerate the delivery of hydrophobic, poorly soluble drugs.

The differences in the size-dependent particle dissolution kinetics are reflected in the nimodipine release profiles from HAMC, and can be exploited in tailoring drug release rates. In the case where the drug is completely solubilized at the beginning of the release process, its release is rapid and governed by Fickian diffusion [Tosun, I., *Modeling in Transport Phenomena, a Conceptual Approach, 2nd ed., Elsevier,* 2007]. In the case of particulate nimodipine, however, release occurs over longer time scales due to the slow dissolution of the drug particles. The release profiles obtained from these particulate formulations are biphasic and dependent on the size of the drug particles introduced into HAMC. Experimental and model analysis of the drug dissolution and release reveals that the biphasic release profiles reflect a rapid release of solubilized drug, followed by a slow dissolution-controlled release of the solid nimodipine. Because the amount of nimodipine that is solubilized at the beginning of the release process varies with the initial drug particle size, the release profiles depend strongly on the size of the drug particles that were used in its preparation. This suggests that HAMC and its homologues can yield highly tunable release profiles that are dependent on how the drug is introduced into the in situ gelling scaffold. Similarly, because the dissolution of the drug particles in MC occurs over the course of several days, these variations indicate that these release profiles can also be adjusted by modulating the time between the preparation and application.

Additionally, the general model developed for predicting the release of nimodipine from HAMC is transferable to other similar systems where sparingly soluble drugs are released from hydrogel scaffolds. The model allows both a better understanding of the mechanism that controls the release of drugs from these systems, as well as to predict drug release behaviour in future studies. Likewise, the use of MC and its homologues in other products, such as foods and personal care formulations, suggests that hydrogels such as HAMC can be used to achieve highly tunable, accelerated delivery of other types of active ingredients, such as hydrophobic neutraceuticals [K. P. Velikov, E. Pelan, Colloidal delivery systems for micronutrients and nutraceuticals. *Soft Matter* 4(10) (2008) 1964-1980], the use of which are limited by their low solubilities.

This description demonstrates that the incorporation of polymeric excipients in an injectable hydrogel can accelerate the release of hydrophobic drugs, and that the addition of MC to water increases the aqueous solubility of sparingly soluble nimodipine. The effect of varying initial particle sizes on the particle dissolution rates to obtain a broad range of release profiles has been demonstrated. These release profiles depend on the method by which the nimodipine is introduced into HAMC, namely the fraction of pre-dissolved drug. Model analysis of these release profiles supports the release mechanism described above, and indicates that an injectable hydrogel bearing MC and its homologues can provide a versatile platform for rapid and controlled release of hydrophobic drugs and other sparingly-soluble compounds.

The disclosures of all publications, patent applications and patents referenced herein are incorporated herein by reference in their entireties.

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features herein before set forth, and as follows in the scope of the appended claims.

What we claim is:

1. A hydrogel matrix comprising: (1) an aqueous solution of methylcellulose, in which particles of at least one hydrophobic therapeutic agent chosen from the group consisting of a drug and a hydrophobic vitamin are predissolved; (2) solid particles of the at least one hydrophobic therapeutic agent; and (3) hyaluronan or a derivative thereof that forms the hydrogel matrix, the solubility of the hydrophobic therapeutic agent being increased in the presence of the methylcellulose, which together with the size of the solid particles determine the sustained release profile of the at least one hydrophobic therapeutic agent from the hydrogel matrix.

2. The hydrogel matrix of claim 1, wherein the matrix comprises an aqueous solution that includes methylcellulose and hyaluronan and wherein the matrix is a room temperature hydrogel matrix.

3. The hydrogel matrix of claim 1, wherein the matrix comprises an aqueous solution comprising methylcellulose and hyaluronan.

4. A hydrogel matrix that provides a biphasic release profile comprising: a blend of (1) a pre-made aqueous solution of methylcellulose or a methyl cellulose derivative chosen from the group consisting of: hydroxypropyl methylcellulose, hydroxypropyl methylcellulose phthalate, 2,3-di-O-methyl-6-O-benzylcellulose, 2,3-di-O-benzyl-6-O-methylcellulose, and hydroxypropyl methylcellulose succinate and solubilized particles of at least one hydrophobic vitamin or hydrophobic drug that are pre-dissolved in the methylcellulose or the methylcellulose derivative prior to blending where the methylcellulose or the methylcellulose derivative enhances the solubility of the solubilized particles of the at least one hydrophobic vitamin or hydrophobic drug; (2) a first solid particulate form of a particle size of the at least one hydrophobic vitamin or hydrophobic drug; and (3) a hyaluronan or a derivative thereof; wherein the blend forms the hydrogel matrix; and wherein the hydrogel matrix provides the solubilized particles of the at least one hydrophobic vitamin or hydrophobic drug as a faster rate than the first solid particle form of a particle size of the at least one hydrophobic vitamin or hydrophobic drug and wherein the water solubility of the at least one hydrophobic vitamin or hydrophobic drug is increased in presence of the methylcellulose or the methylcellulose derivative and wherein the solubilized particles and the particle size of the first solid particulate form of the at least one hydrophobic vitamin or hydrophobic drug create a biphasic release of the at least one hydrophobic vitamin or hydrophobic drug.

5. The hydrogel matrix of claim 4, wherein the solubilized particles of the at least one hydrophobic vitamin or hydrophobic drug are fully released within 8 hours of administration of the hydrogel matrix.

6. The hydrogel matrix of claim 4, wherein the blend further comprises a second solid particulate form of a second particle size of the at least one hydrophobic vitamin or hydrophobic drug wherein the second particle size is different from the first particle size.

7. The hydrogel matrix of claim 6, wherein the first solid particulate form and the second solid particulate form are the same at least one hydrophobic vitamin or hydrophobic drug.

8. The hydrogel matrix as claimed in claim 1, wherein the hyaluronan or a derivative thereof comprises from about 100 to about 7,000 kg/mol and the methylcellulose comprises from about 2 to about 3,000 kg/mol.

9. The hydrogel matrix as claimed in claim 1, wherein the ratio of hyaluronan or a derivative thereof to the methylcellulose comprises from about 1:20 to about 1:1 w/w and wherein the solid particulate form comprises both microparticles and nanoparticles.

10. The hydrogel matrix as claimed in claim 1, wherein the amount of hyaluronan or a derivative thereof comprises from about 0.5% to about 5.0% by weight and the methylcellulose comprises from about 1.0% to about 20% by weight of the matrix and wherein the solid particulate form comprises both microparticles and nanoparticles.

11. The hydrogel matrix as claimed in claim 1, wherein the amount of hyaluronan or a derivative thereof comprises form a bout 0.5% to about 5.0% by weight and the methylcellulose comprises from about 1.0% to about 10% by weight of the matrix and wherein the solid particulate form comprises both microparticles and nanoparticles.

12. The hydrogel matrix as claimed in claim 1, wherein the hydrophobic vitamin or hydrophobic drug is sparingly soluble hydrophobic vitamin or hydrophobic drug comprising from about 0.0001 to about 30 wt %, based on the matrix.

13. The hydrogel matrix as claim in claim 12, wherein the sparingly soluble hydrophobic vitamin or hydrophobic drug comprises from about 0.1 to about 30 wt %, based upon the matrix.

14. The hydrogel matrix as claimed in claim 1, wherein the aqueous solution is selected from the group consisting of: water, saline, artificial cerebrospinal, and buffered solutions and wherein the solid particulate form comprises both microparticles and nanoparticles.

15. The hydrogel matrix as claimed in claim 1, wherein the at least one hydrophobic vitamin or hydrophobic drug is selected from the group comprising aloxiprin, auranofin, azapropazone, benorylate, diflunisal, etodolac, fenbufen, fenoprofen calcium, flurbiprofen, ibuprofen, indomethacin, ketoprofen, meclofenamic acid, mefenamic acid, nabumetone, naproxen, oxyphenbutazone, phenylbutazone, piroxicam, sulindac, albendazole, bepheniudm hydroxynaphthoate, cambendazole, dichlorophen, ivermectin, mebendazole, oxamniquine, oxfendazole, oxantel embonate, praziquantel, pyrantel embonate, thiabendazole, amiodarone HCI, disopyramide, flecamide acetate, quinidine sulphate, benethamine penicillin, cinoxacin, ciprofloxacin HCI, clarithromycin, clofazimine, cloxacillin, demeclocycline, doxycycline, erythromycin, ethionamide, imipenem, nalidixic acid, nitrofurantoin, rifampicin, spiramycin, sulphabenzamide, sulphadoxine, sulphamerazine, sulphacetamide, sulphadiazine, sulphafurazole, sulphamethoxazole, sulphapyridine, tetracycline, trimethoprim, dicoumarol, dipyridamole, nicoumalone, phenindione, amoxapine, maprotiline HCI, mianserin HCL, nortriptyline HCI, trazodone HCL, trimipramine maleate, acetohexamide, chlorpropamide, glibenclamide, gliclazide, glipizide, tolazamide, tolbutamide, beclamide, carbamazepine, clonazepam, ethotoin, methoin, methsuximide, methylphenobarbitone, oxcarbazepine, paramethadione, phenacemide, phenobarbitone, phenyloin, phensuximide, primidone, sulthiame, valproic acid, amphotericin, butoconazole nitrate, clotrimazole, econazole nitrate, fluconazole, flucytosine, griseofulvin, itraconazole, ketoconazole, miconazole, natamycin, nystatin, sulconazole nitrate, terbinafine HCI, terconazole, tioconazole, undecenoic acid, allopurinol, probenecid, sulphin-pyrazone, amlodipine, benidipine, darodipine, dilitazem HCI, diazoxide, felodipine, guanabenz acetate, isradipine, minoxidil, nicardipine HCI, nifedipine, nimodipine, phenoxybenzamine HCI, prazosin HCL, reserpine, terazosin HCL, amodiaquine, chloroquine, chlorproguanil HCI, halofantrine HCI, mefloquine HCI, proguanil HCI, pyrimethamine, quinine sulphate, dihydroergotamine mesylate, ergotamine tartrate, methysergide maleate, pizotifen maleate, sumatriptan succinate, atropine, benzhexyl HCI, biperiden, ethopropazine HCI, hyoscyamine, mepenzolate bromide, oxyphencylcimine HCI, tropicamide, aminoglutethimide, amsacrine, azathioprine, busulphan, chlorambucil, cyclosporin, dacarbazine, estramustine, etoposide, lomustine, melphalan, mercaptopurine, methotrexate, mitomycin, mitotane, mitozantrone, procarbazine HCI, tamoxifen citrate, testolactone, benznidazole, clioquinol, decoquinate, diiodohydroxyquinoline, diloxanide furoate, dinitolmide, furzolidone, metronidazole, nimorazole, nitrofurazone, ornidazole, tinidazole, carbimazole, propylthiouracil, alprazolam, amylobarbitone, barbitone, bentazepam, bromazepam, bromperidol, brotizolam, butobarbitone, carbromal, chlordiazepoxide, chlormethiazole, chlorpromazine, clobazam, clotiazepam, clozapine, diazepam, droperidol, ethinamate, flunanisone, flunitrazepam, fluopromazine, flupenthixol decanoate, fluphenazine decanoate, flurazepam, haloperidol, lorazepam, lormetazepam, medazepam, meprobamate, methaqualone, midazolam, nitrazepam, oxazepam, pentobarbitone, perphenazine pimozide, prochlorperazine, sulpiride, temazepam, thioridazine, triazolam, zopiclone, acebutolol, alprenolol, atenolol, labetalol, metoprolol, nadolol, oxprenolol, pindolol, propranolol, amrinone, digitoxin, digoxin, enoximone, lanatoside C, medigoxin, beclomethasone, betamethasone, budesonide, cortisone acetate, desoxymethasone, dexamethasone, fludrocortisone acetate, flunisolide, flucortolone, fluticasone propionate, hydrocortisone, methylprednisolone, prednisolone, prednisone, triamcinolone, acetazolamide, amiloride, bendrofluazide, bumetanide, chlorothiazide, chlorthalidone, ethacrynic acid, frusemide, metolazone, spironolactone, triamterene, bromocriptine mesylate, lysuride maleate, bisacodyl, cimetidine, cisapride, diphenoxylate HCI, domperidone, famotidine, loperamide, mesalazine, nizatidine, omeprazole, ondansetron HCL, ranitidine HCI, sulphasalazine, acrivastine, astemizole, cinnarizine, cyclizine, cyproheptadine HCI, dimenhydrinate, flunarizine HCI, loratadine, meclozine HCI, oxatomide, terfenadine, bezafibrate, clofibrate, fenofibrate, gemfibrozil, probucol, amyl nitrate, glyceryl trinitrate, isosorbide dinitrate, isosorbide mononitrate, pentaerythritol tetranitrate, betacarotene, vitamin A, vitamin B2, vitamin D, vitamin E, vitamin K, codeine, dextropropyoxyphene, diamorphine, dihydrocodeine, meptazinol, methadone, morphine, nalbuphine, pentazocine, clomiphene citrate, danazol, ethinyl estradiol, medroxyprogesterone acetate, mestranol, methyltestosterone, norethisterone, norgestrel, estradiol, conjugated oestrogens, progesterone, stanozolol, stibestrol, testosterone, tibolone, amphetamine, dexamphetamine, dexfenfluramine, fenfluramine, mazindol, and mixtures thereof and wherein the hydrogel matrix has an altered chemical functionality by the addition of at least one functional group to the hyaluronan or derivative thereof or the methylcellulose selected from the group consisting of carboxylic acid, primary amine, aldehyde, hydrazide, maleimide, thiol, furan, alkyne, azide, alkene, urethane, and primary alcohol.

16. The hydrogel matrix as claimed in claim 1, wherein the hydrogel matrix has an altered rate of degradation by crosslinking the hyaluronan or the derivative thereof or by increasing the hydrophobicity of the hyaluronan or the derivative thereof.

17. The hydrogel matrix as claimed in claim 1, wherein a charge stabilizer is added to promote an interaction between the methylcellulose and the hydrophobic vitamin or hydrophobic drug and wherein the solid particles of the at least one hydrophobic vitamin or hydrophobic drug is covalently bonded to the hyaluronan or methylcellulose.

18. The hydrogel matrix as claimed in claim 1, wherein the derivative of hyaluronan are esters of hyaluronan resulting from esterification with alcohols chosen from the group consisting of: aliphatic alcohols, cycloaliphatic alcohols and heterocyclic alcohols.

* * * * *

UNITED STATES PATENT AND TRADEMARK OFFICE
CERTIFICATE OF CORRECTION

| | | |
|---|---|---|
| PATENT NO. | : 9,205,047 B2 | Page 1 of 3 |
| APPLICATION NO. | : 12/785083 | |
| DATED | : December 8, 2015 | |
| INVENTOR(S) | : Shoichet et al. | |

It is certified that error appears in the above-identified patent and that said Letters Patent is hereby corrected as shown below:

In the specification

*Col. 1, line 52
"Iphenyl" should be – phenyl –

*Col. 3, line 11
Delete "/ [virgule]" after – (2003) –

*Col. 4, line 56
"solubilises" should be – solubilizes –

*Col. 4, lines 66-67
"solubilising" should be – solubilizing –

*Col. 5, line 5
"solubilised" should be – solubilized –

*Col. 5, line 18
"solubilising" should be – solubilizing –

*Col. 5, line 23
"solubilised" should be – solubilized –

*Col. 5, line 37
"solubilised" should be – solubilized –

*Col. 5, line 49
"solubilising" should be – solubilizing –

Signed and Sealed this
Nineteenth Day of April, 2016

Michelle K. Lee
*Director of the United States Patent and Trademark Office*

CERTIFICATE OF CORRECTION (continued)
U.S. Pat. No. 9,205,047 B2

\*Col. 5, line 53
"solubilised" should be – solubilized –

\*Col. 5, line 54
"therapeuti" should be – therapeutic –

\*Col. 7, line 63
"solubilisation" should be – solubilization –

\*Col. 8, line 1
"solubilising" should be – solubilizing –

\*Col. 9, line 19
"2,3-di-O– benzylcellulose" should be – 2,3-di-O-benzylcellulose –

\*Col. 9, line 45
"calcim" should be – calcium –

\*Col. 9, line 54
"sulphate:" should be – sulphate; –

\*Col. 9, line 66
"tolbutamide," should be – tolbutamide; –

\*Col. 10, lines 41-42
"beta-blockers," should be – beta-blockers: –

\*Col. 11, line 1
"hormones;" should be – hormones: –

\*Col. 11, line 24
"are" should be – of –

\*Col. 11, line 28
"solubilisation" should be – solubilization –

\*Col. 11, line 37
"100-☐m" should be – 100-μm –

\*Col. 14, line 38
" ~0(10 μm)" should be – ~O(10 μm) –

\*Col. 14, line 65
"$C_A^{sat}$" should be – $C_A^{Sat}$ –

*Col. 15, line 26
"<4 to <40" should be — $\leq 4$ to $\leq 40$ —

*Col. 17, line 39
"$C_A^{sat}$" should be — $C_A^{Sat}$ —

*Col. 18, line 1
"$C_A^{sat}$" should be — $C_A^{Sat}$ —

*Col. 18, line 55
"$C_A^{sat}$" should be — $C_A^{Sat}$ —

*Col. 19, line 14
"$C_A^{sat}$" should be — $C_A^{Sat}$ —

*Col. 20, line 23
"behaviour" should be — behavior —

In the claims

*Col. 21, claim 4, line 29
"as" should be — at —

*Col. 21, claim 11, line 67; Col. 22, line 1
"forma bout" should be — from about —

*Col. 22, claim 13, line 9
"claim" (1st occurrence) should be — claimed —

*Col. 22, claim 15, line 25
"bepheniudm" should be — bephenium —

*Col. 24, claim 18, line 27
"derivative" should be — derivatives —